US008133727B2

(12) United States Patent
Luo et al.

(10) Patent No.: US 8,133,727 B2
(45) Date of Patent: Mar. 13, 2012

(54) IN VITRO HUMAN B LYMPHOPOIESIS CULTURE SYSTEM

(75) Inventors: Xin Luo, Pasadena, CA (US); Lili Yang, Arcadia, CA (US); David Baltimore, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 12/622,379

(22) Filed: Nov. 19, 2009

(65) Prior Publication Data

US 2010/0203630 A1 Aug. 12, 2010

(51) Int. Cl.
*C12N 5/08* (2006.01)
*C12N 5/00* (2006.01)
*C12N 5/02* (2006.01)

(52) U.S. Cl. ............ 435/372.2; 435/373; 435/375; 435/377

(58) Field of Classification Search ................ None
See application file for complete search history.

(56) References Cited

U.S. PATENT DOCUMENTS

2007/0116690 A1 5/2007 Yang et al.

OTHER PUBLICATIONS

International Search Report and Written Opinion dated Aug. 13, 2010 in Application No. PCT/US2009/065217, filed Nov. 19, 2009.
Luo et al., Engineering human hematopoietic stem/progenitor cells to produce a broadly neutralizing anti-HIV antibody after in vitro maturation to human B lymphocytes, Blood, Feb. 12, 2009, vol. 113, Issue 7, pp. 1422-1431.
Arce, et al., "CD38 Low IgG-secreting Cells are Precursors of Various CD38 High-expressing Plasma Cell Populations," *J Leukoc Biol*, (2004) 75:1022-1028.
Barbas, et al., "Molecular Profile of an Antibody Response to HIV-1 as Probed by Combinatorial Libraries," *J Mol Biol*, (1993) 230:812-823.
Binley, et al., "Comprehensive Cross-clade Neutralization Analysis of a Panel of Anti-human Immunodeficiency Virus Type 1 Monoclonal Antibodies," *J Virol*, (2004) 78:13232-13252.
Brussel, et al., "Alu-LTR Real-time Nested PCR Assay for Quantifying Integrated HIV-1 DNA," *Methods Mol Biol*, (2005) 304:139-154.
Burton, et al., "Antibody vs. HIV in a Clash of Evolutionary Titans," *Proc Natl Acad Sci U S A*, (2005) 102:14943-149.
Burton, et al., "Efficient Neutralization of Primary Isolates of HIV-1 by a Recombinant Human Monoclonal Antibody," *Science*, (1994) 266:1024-1027.
Butler, et al., "A Quantitative Assay for HIV DNA Integration In Vivo," *Nat Med*, (2001) 7:631-634.
Chen, et al., "Gene Rearrangement and B-cell Development," *Curr Opin Immunol*, (1993) 5:194-200.
Douek,et al., "The Rational Design of an AIDS Vaccine," *Cell*, (2006) 124:677-681.
Fluckiger, et al., "In Vitro Reconstitution of Human B-cell Ontogeny: From CD34+ Multipotent Progenitors to Lg-secreting Cells," *Blood*, (1998) 92:4509-4520.
Frecha, et al., "Efficient and Stable Transduction of Resting B Lymphocytes and Primary Chronic Lymphocyte Leukemia Cells Using Measles Virus gp Displaying Lentiviral Vectors," *Blood*, (2009) 114: 3173-80.
Gauduin, et al., "Passive Immunization with a Human Monoclonal Antibody Protects Hu-PBLSCID Mice Against Challenge by Primary Isolates of HIV-1," *Nat Med*, (1997) 3:1389-1393.
Graham, et al. "A new technique for the assay of infectivity of human adenovirus 5 DNA," *Virol.* (1973) 52:456-467.
Grande, et al., "Transcriptional Targeting of Retroviral Vectors to the Erythroblastic Progeny of Transduced Hematopoietic Stem Cells," *Blood*, (1999) 93: 3276-3285.
Grassinger, et al., "Differentiation of Hematopoietic Progenitor Cells Towards the Myeloid and B-lymphoid Lineage by Hepatocyte Growth Factor (HGF) and Thrombopoietin (TPO) Together with Early Acting Cytokines," *Eur J Haematol*, (2006) 77:134-144.
Hao, et al., "A Functional Comparison of CD34 _ CD38- Cells in Cord Blood and Bone Marrow," *Blood*, (1995) 86:3745-3753.
Hirayama, et al., "The Flt3 Ligand Supports Proliferation of Lymphohematopoietic Progenitors and Early B-lymphoid Progenitors," *Blood*, (1995) 85:1762-1768.
Huggins, et al., "CpG DNA and Plasma Cell Differentiation of CD27-naive Human B Cells," *Blood*, (2007) 109: 1611-1619.
Iwasaki, et al., "Myeloid Lineage Commitment from the Hematopoietic Stem Cell," *Immunity*, (2007) 26:726-740. 28.
Karlsson, et al., "The Challenges of Eliciting Neutralizing Antibodies to HIV-1 and to Influenza Virus," *Nat Rev Microbiol*, (2008) 6:143-155.
Kehry, et al., "CD40-mediated Signaling in B cells: Balancing Cell Survival, Growth, and Death," *J Immunol*, (1996) 156: 2345-2348.
Kessler, et al., "Recombinant Human Monoclonal Antibody IgG1b12 Neutralizes Diverse Human Immunodeficiency Virus Type 1 Primary Isolates," *AIDS Res Hum Retroviruses*, (1997) 13:575-582.
Lane, et al., "Abnormalities of B-cell Activation and Immunoregulation in Patients with the Acquired Immunodeficiency Syndrome," *N Engl J Med*, (1983) 309:453-458.
Lanzavecchia, et al., "Understanding and Making Use of Human Memory B Cells," *Immunol Rev.* (2006) 211:303-309.
Lazar, et al., "Engineered Antibody Fc Variants with Enhanced Effector Function," *Proc Natl Acad Sci U S A*, (2006) 103:4005-4010.
Lens, et al., "A Dual Role for Both CD40-ligand and TNF-alpha in Controlling Human B cell death," *J Immunol*, (1996) 156:507-514.
Letvin, et al., "Progress and Obstacles in the Development of an AIDS Vaccine," *Nat Rev Immunol*, (2006) 6:930-939.
Lin, et al., "Blimp-1-dependent Repression of Pax-5 is Required for Differentiation of B cells to Immunoglobulin M-secreting Plasma Cells," *Mol Cell Biol*, (2002) 22:4771-4780.
Lois, et al., "Germline Transmission and Tissue-specific Expression of Transgenes Delivered by Lentiviral Vectors," *Science*, (2002) 295:868-872.
Marodon, et al., "Specific Transgene Expression in Human and Mouse CD4_ Cells Using Lentiviral Vectors with Regulatory Sequences from the CD4 Gene," *Blood*, (2003) 101:3416-3423.
Messner, et al., "Assessment and Characterization of Hemopoietic Stem Cells," *Stem Cells*, (1995) 13(suppl 3):13-18.

(Continued)

*Primary Examiner* — Michail Belyavskyi
(74) *Attorney, Agent, or Firm* — Knobbe, Martens, Olson & Bear LLP

(57) ABSTRACT

The present disclosure relates to systems, methods and compositions for the generation of antibody-producing B cells in vitro. Some embodiments are related to an in vitro system for generating antibody-producing B cells from hematopoietic stem/progenitor cells (HSPCs).

22 Claims, 17 Drawing Sheets

OTHER PUBLICATIONS

Mizuma, et al., "Serum IgD Elevation is an Early Marker of B Cell Activation During Infection with the Human Immunodeficiency Viruses," *Clin Exp Immunol*, (1987) 68:5-14.

Nishimura, et al., "Transfer of Neutralizing IgG to Macaques 6 h but not 24 h After SHIV Infection Confers Sterilizing Protection: Implications for HIV-1 Vaccine Development," *Proc Natl Acad Sci U S A*, (2003) 100: 15131-15136.

Ohkawara, et al., "Culture System for Extensive Production of CD19_IgM_Cells by Human Cord Blood CD34_Progenitors," *Leukemia*, (1998) 12:764-771.

Pantophlet, et al., "Fine Mapping of the Interaction of Neutralizing and Nonneutralizing Monoclonal Antibodies with the CD4 Binding Site of Human Immunodeficiency Virus Type 1 gp120," *J Virol*, (2003) 77:642-658.

Pantophlet, et al., "GP120: Target for Neutralizing HIV-1 Antibodies," *Annu Rev Immunol*, (2006) 24:739-769.

Parren, et al., "Antibody Protects Macaques Against Vaginal Challenge with a Pathogenic R5 Simian/Human Immunodeficiency Virus at Serum Levels Giving Complete Neutralization In Vitro," *J Virol*, (2001) 75:8340-8347.

Parren, et al., "Protection Against HIV-1 Infection in Hu-PBL-SCID Mice by Passive Immunization with a Neutralizing Human Monoclonal Antibody Against the gp120 CD4-binding Site," *AIDS*, (1995) 9:F1-F6.

Pear, et al., "Production of High-titer Helper-free Retroviruses by Transient Transfection," *Proc Natl Acad Sci U S A*, (1993) 90:8392-8396.

Pitisuttithum, et al., "Randomized, Double-blind, Placebo-controlled Efficacy Trial of a Bivalent Recombinant Glycoprotein 120 HIV-1 Vaccine Among Injection Drug Users in Bangkok, Thailand," *J Infect Dis*, (2006) 194:1661-1671.

Saeland, et al., "Interleukin-7 Induces the Proliferation of Normal Human B-cell Precursors," *Blood*, (1991) 78:2229-2238.

Schatzlein et al., "Non-viral vectors in cancer gene therapy: principles and progress." *Anticancer Drugs*, (2001) 12:275-304.

Selvarajah, et al., "Comparing Antigenicity and Immunogenicity of Engineered gp120," *J Virol*, (2005) 79:12148-12163.

Szymczak, et al., "Correction of Multi-gene Deficiency In Vivo Using a Single "Self-cleaving" 2A Peptide-based Retroviral Vector," *Nat Biotechnol*, (2004) 22:589-594.

Van De Winkel, et al., "Immunotherapeutic Ootential of Bispecific Antibodies," *Immunol Today*, (1997) 18:562-564.

Veazey, et al., "Prevention of Virus Transmission to Macaque Monkeys by a Vaginally Applied Monoclonal Antibody to HIV-1 gp120," *Nat Med*, (2003) 9:343-346.

Watkins, et al., "Nonhuman Primate Models and the Failure of the Merck HIV-1 Vaccine in Humans," *Nat Med*, (2008) 14:617-621.

Werner, et al., "B-cellspecific Transgene Expression Using a Self-inactivating Retroviral Vector with Human CD19 Promoter and Viral Post-transcriptional Regulatory Element," Gene Ther. (2004) 11:992-1000.

Wigler, et al., "DNA-mediated transfer of the adenine phosphoribosyltransferase locus into mammalian cells," *Proc. Natl. Acad. Sci. USA*, (1979) 76:1373-1376.

Wyatt, et al., "The HIV-1 Envelope Glycoproteins: Fusogens, Antigens, and Immunogens," *Science*, (1998) 280:1884-1888.

Yang, et al., "Long-term In Vivo Provision of Antigen-specific T Cell Immunity by Programming Hematopoietic Stem Cells," *Proc Natl Acad Sci U S A*, (2005) 102:4518-4523.

Zwick, et al., "Neutralization Synergy of Human Immunodeficiency Virus Type 1 Primary Isolates by Cocktails of Broadly Neutralizing Antibodies," *J Virol*, (2001) 75:12198-12208.

C

IN VITRO HUMAN B LYMPHOPOIESIS CULTURE SYSTEM

RELATED APPLICATIONS

The present application claims priority under 35 U.S.C. §119(e) to U.S. Provisional Application No. 61/199,932, filed on Nov. 21, 2008, which is herein expressly incorporated by reference.

REFERENCE TO SEQUENCE LISTING

The present application is being filed along with a Sequence Listing in electronic format. The Sequence Listing is provided as a file entitled SEQLISTING.TXT, created Nov. 19, 2009, which is 4.0 Kb in size. The information in the electronic format of the Sequence Listing is incorporated herein by reference in its entirety.

BACKGROUND OF THE INVENTION

1. Field of the Invention

The present application relates generally to the fields of immunology and gene delivery. More particularly, the application relates to an in vitro human B lymphopoiesis culture system for programming human B cells to make an antibody of interest.

2. Description of the Related Art

Antibodies are naturally occurring proteins produced by immune systems that play an important role in fighting infections and eliminating pathogenic factors. Antibodies exert their functions by binding protein or non-protein antigens and triggering a defensive response.

B cells are lymphocytes that play a major role in antibody-producing. During normal hematopoiesis, B-cell populations are generated from hematopoietic stem cells in the bone marrow and become activated. Upon activation, the B cells begin to differentiate into more specialized cells, including antibody-secreting plasmablasts and plasma cells.

Accordingly, it is desirable to develop an efficient in vitro culture system that supports human B-lineage development and facilitates the differentiation of B cells to produce any antibody of interest.

SUMMARY OF THE INVENTION

The present application provides systems, methods and compositions for generating antibody-producing B cells in vitro. Antibody-producing B cells generated according to the systems and methods described herein have a wide variety of utilities, including therapeutic, diagnostic, industrial, forensics, and environmental applications. Some non-limiting examples of utilities are: priming an organism's immune response against a pathogen; providing an immune response against a particular disease or disorder, for example, a pathogenic infection, such as an HIV infection, or cancer; and detecting a particular disease or disorder and/or monitoring the progression of a particular disease or disorder. The antibody produced according to the system and methods described herein can be used in applications, such as identifying presence of organisms and/or antigens (for example, polypeptides, carbohydrates, lipids or nucleic acids) in forensic/environmental samples, detection of activated state of an enzyme, and production of purified proteins.

In one aspect of the present application, methods for generating B cells that produce an antibody of interest from a population of hematopoietic stem/progenitor cells (HSPCs) in vitro are provided. In some embodiments, the methods comprise: (a) contacting a population of hematopoietic stem/progenitor cells (HSPCs) in vitro with a polynucleotide delivery system, where the polynucleotide delivery system comprises a polynucleotide encoding an antibody of interest; (b) co-culturing the HSPCs with a population of first supporting cells expressing one or more B-lineage growth factors; (c) co-culturing the CD19$^+$ cells obtained in step (b) with a population of second supporting cells expressing CD40L in the presence of one or more B-cell activators. In other embodiments, the methods further comprise culturing the HSPCs in the presence of one or more B-cell priming factors before step (b). Step (b) can be carried out, for example, until at least about 20% of the HSPCs become CD19$^+$μ$^+$. Similarly, step (c) can be carried out, for example, until at least about 20% of the CD19$^+$μ$^+$ cells become B cells that produce the antibody of interest.

In another aspect of the present application, methods for generating a population of B cells in vitro are provided. In some embodiments, the methods comprise: (a) culturing a population of HSPCs in the presence of one or more B-cell priming factors, (b) co-culturing the HSPCs with a population of first supporting cells expressing one or more B-lineage growth factors, typically until at least about 20% of the HSPCs become CD19$^+$μ$^+$; (c) co-culturing the CD19$^+$μ$^+$ cells obtained in step (b) with a population of second supporting cells expressing CD40L in the presence of one or more B-cell activators. Step (c) may be carried out, for example, until at least about 20% of the CD19$^+$μ$^+$ cells become activated B cells.

In another aspect of the present application, methods for generating antibody-producing B cells from a population of target cells in vitro are provided. In some embodiments, the methods comprise: (a) contacting a population of target cells in vitro a polynucleotide delivery system, where the polynucleotide delivery system comprises a polynucleotide encoding an antibody of interest; (b) co-culturing the target cells with a population of first supporting cells expressing one or more B-lineage growth factors, for example until at least about 20% of the target cells become CD19$^+$μ$^+$V$_{preB}^+$ or CD19$^+$μ$^+$κ/λ$^+$; (c) co-culturing the CD19$^+$μ$^+$V$_{preB}^+$ and CD19$^+$μ$^+$κ/λ$^+$ cells obtained in step (b) with a population of second supporting cells expressing CD40L in the presence of one or more B-cell activators, for example until at least about 20% of the CD19$^+$μ$^+$V$_{preB}^+$ and CD19$^+$μ$^+$κ/λ$^+$ cells become B cells that produce the antibody of interest. In some embodiments, at most about 25% of the population of target cells is pre-B and immature B cells. In other embodiments, at most about 20% of the population of target cells are pre-B and immature B cells.

using different promoter (MH and EEK) and different transgene (GFP and b12). The percentages shown are those of total live cells.

Figure 7:
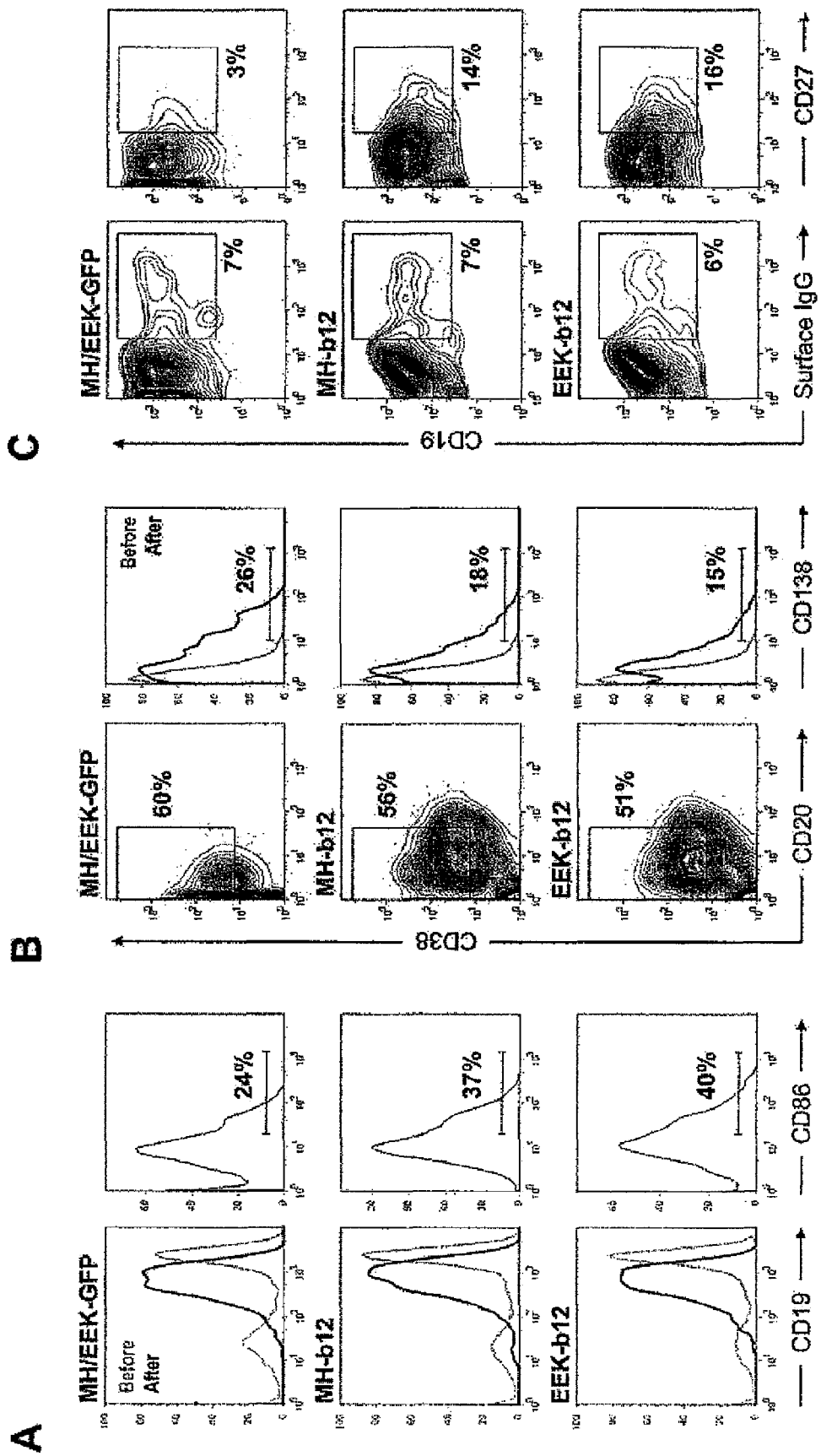
FIG. 7A shows the comparison of CD19 and CD86 expression before (lighter lines) and after (darker lines) stage 3. Cells from stage 2 were transferred onto the MS40L-low monolayer and incubated in the presence of IL-2 (10 ng/mL), IL-10 (100 ng/mL), and CpG DNA (2 μM) for 2 to 3 weeks.
FIG. 7B shows the generation of plasmablasts (CD20$^-$CD38$^+$CD138$^-$) and plasma cells (CD20$^-$CD38$^+$CD138$^+$)
Figure 7:
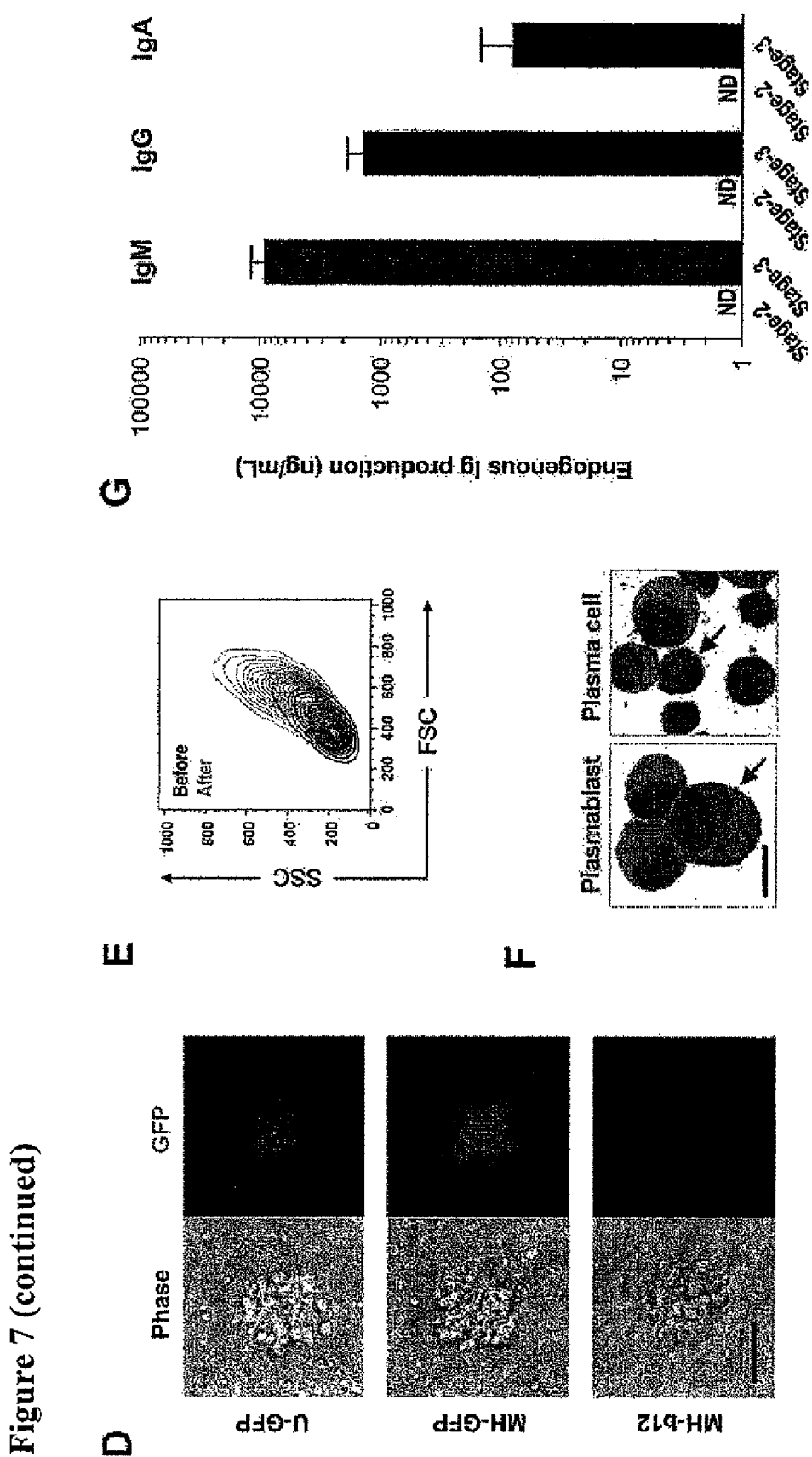

FIG. 7C shows the generation of class-switched B cells (surface IgG$^+$) and memory B cells (CD19$^+$CD27$^+$). The percentages shown are those of CD19$^+$ cells.

FIG. 7D shows the proliferation of B cells during stage 3 and the formation of clusters on the MS40L-low monolayer in the phase-contrast and fluorescent images. Bar represents 25 μm. Cell clusters were visualized by an epifluorescence microscope equipped with a GFP filter set.

FIG. 7E are representative forward (FSC) and side (SSC) scatter graphs of CD19$^+$ cells before (darker traces) and after (lighter traces) stage 3. The cells after stage 3 were larger in size and more granular than those before stage 3.

FIG. 7F are representative Wright stain images of plasmablasts and plasma cells. The plasmablasts and plasma cells are indicated by arrows. Bar represents 5 μm.

FIG. 7G shows endogenous levels of IgM, IgG, and IgA production by cells carrying no virus or the GFP transgene at the end of stage 2 and stage 3. The antibody productions were assayed using ELISA. ND indicates not detectable.

Figure 8:
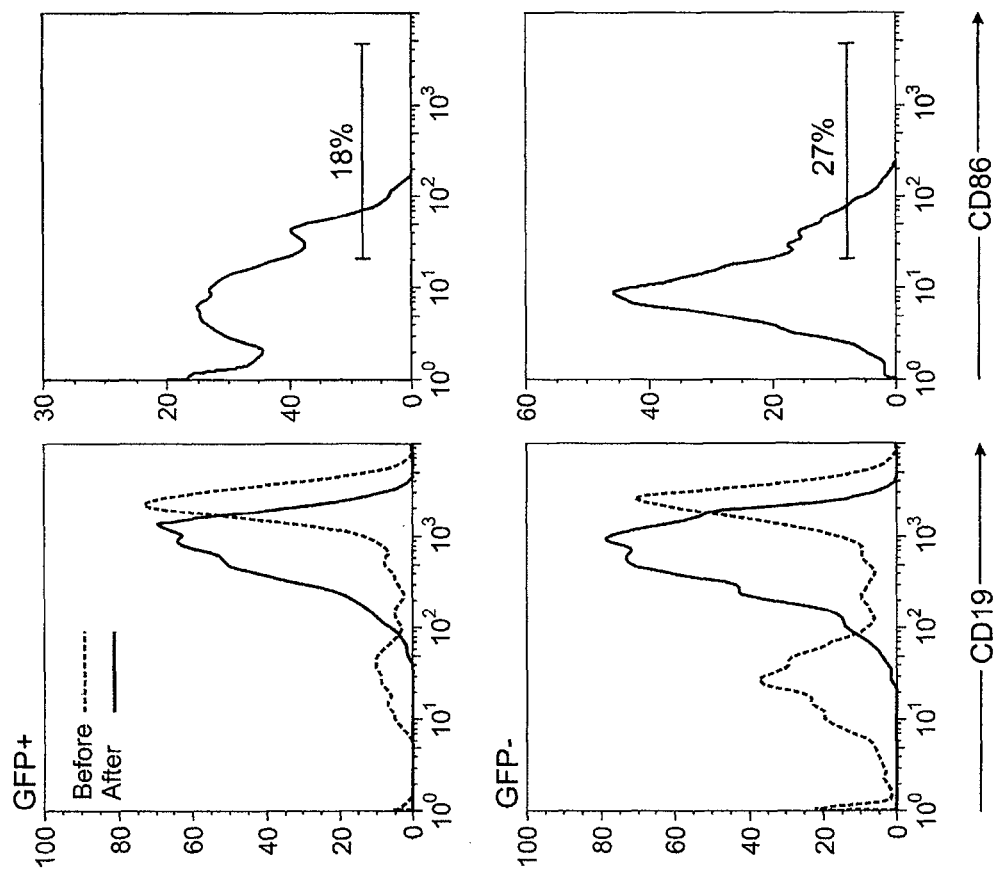
Figure 8:
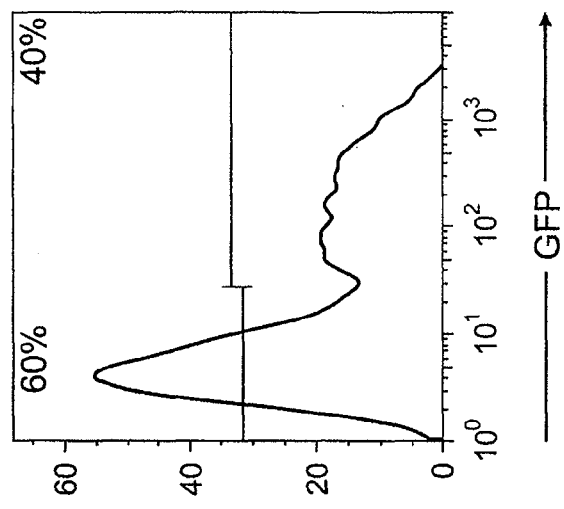
Figure 8:
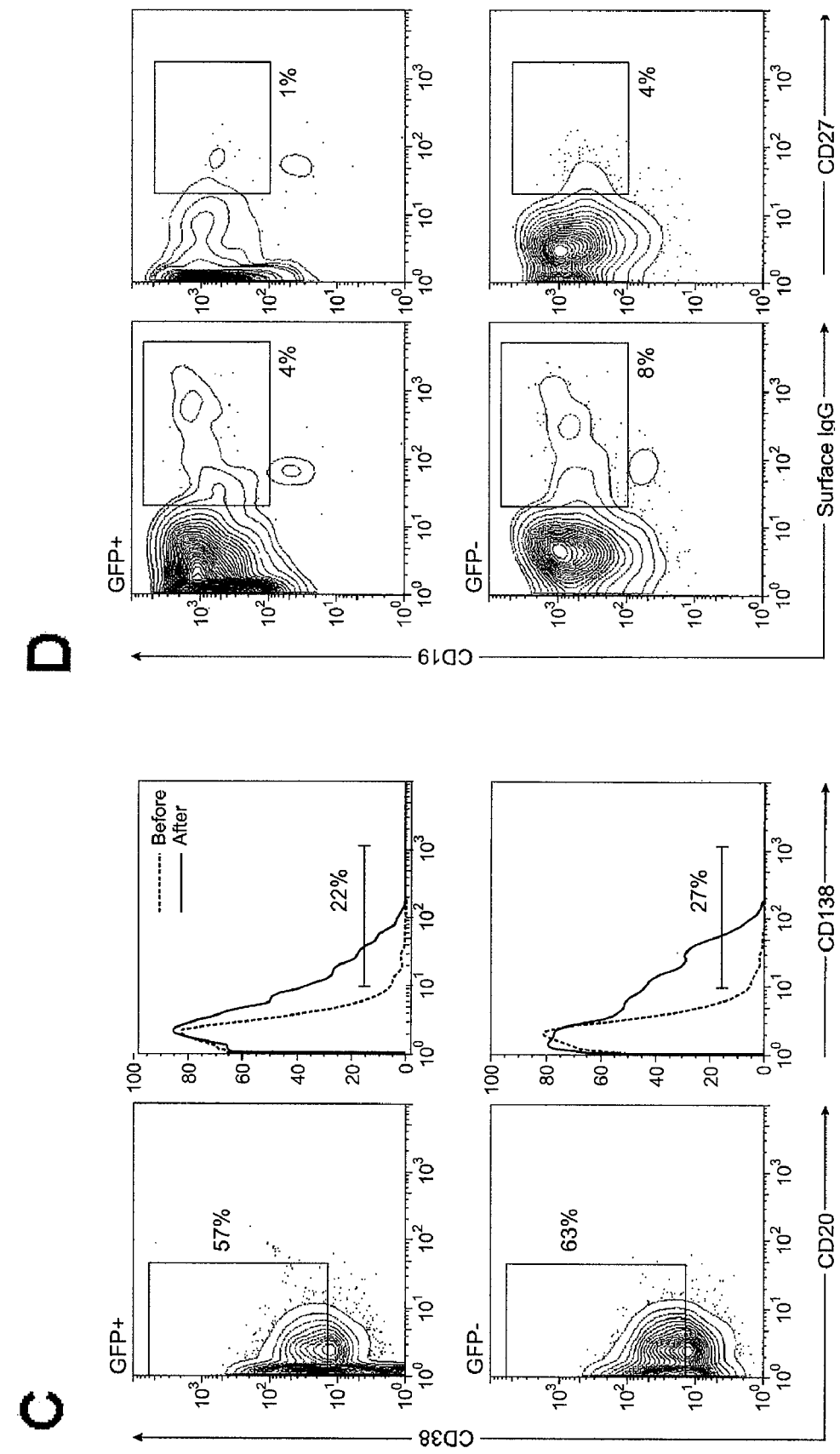

FIG. 8A shows the GFP expressions in B cells carrying MH-b12 or EEK-b12 transgene during stage 3.

FIG. 8B shows the changes in the expression of CD19 and CD86 on cells from pre-stage 3 to after-stage 3.

FIG. 8C shows the generation of plasmablasts (CD20$^-$CD38$^+$CD138$^{-/low}$) and plasma cells (CD20$^-$CD38$^+$CD138$^+$) regardless of transgene GFP during stage 3. The percentages shown are those of total live cells.

FIG. 8D shows the generation of class-switched B cells (surface IgG$^+$) and memory B cells (CD19$^+$CD27$^+$) regardless of transgene GFP during stage 3. The percentages shown are those of CD19$^-$ cells.

Figure 9:
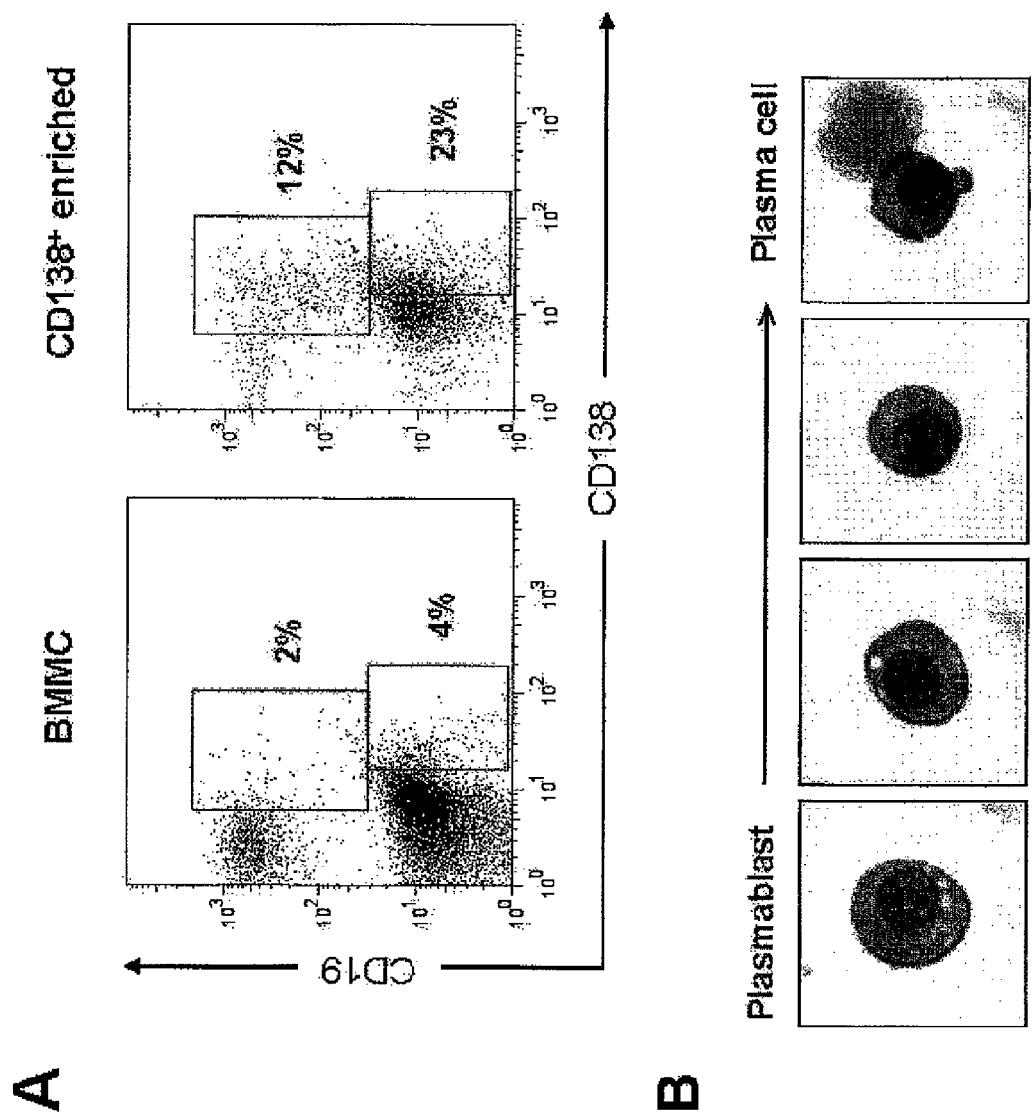

FIG. 9A shows CD138$^+$-enriched cell population from normal human bone marrow mononuclear cells (BMMC) during stage 3.

FIG. 9B shows morphology of normal human plasmablasts and plasma cells.

Figure 10:
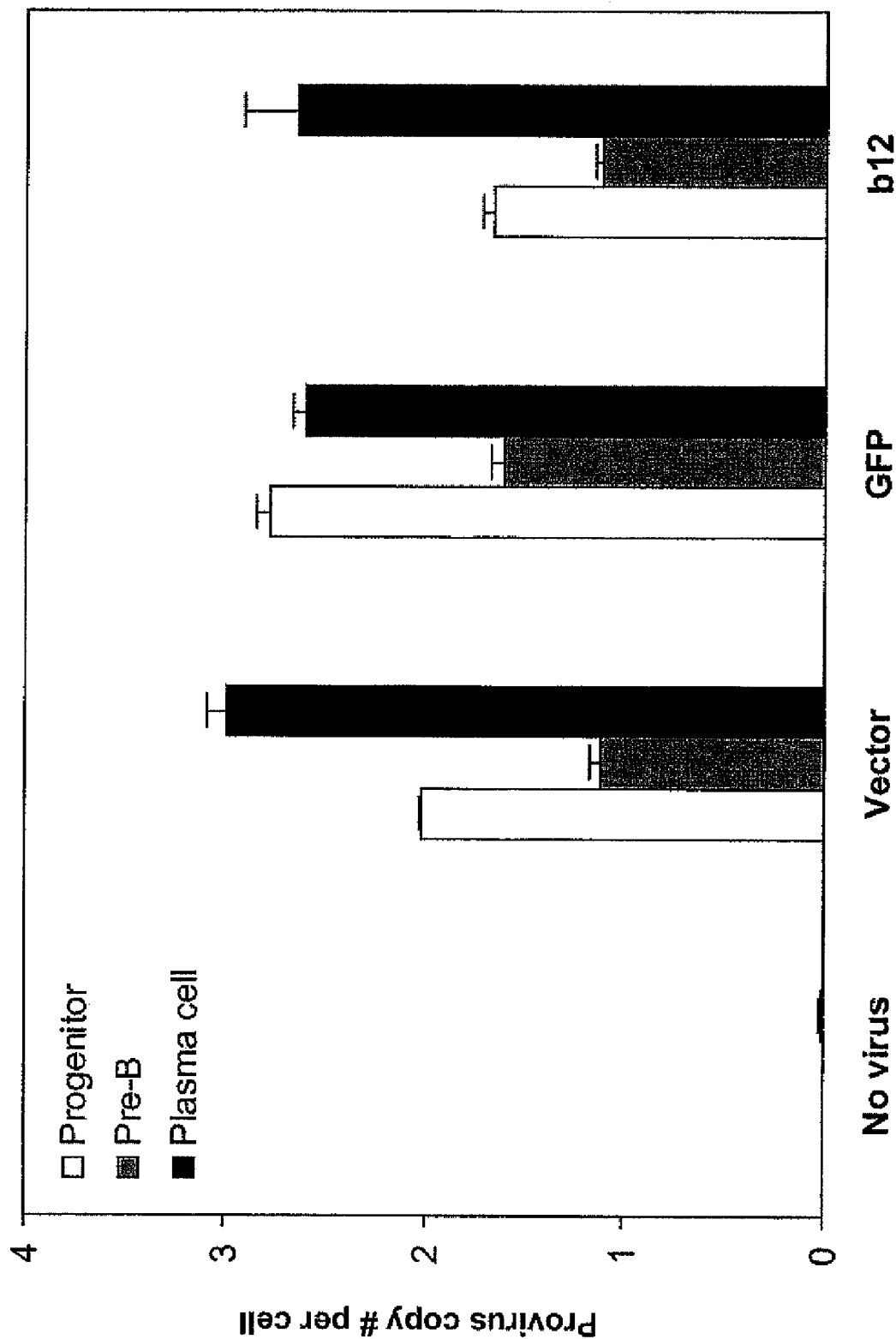

FIG. 10 shows stable integration of the lentivirus maintained throughout human B-cell development in vitro. Genomic DNA from cells at week 2 and week 4 of stage 2 (representing progenitor and pre-B stages, respectively) and at the end of stage 3 (representing plasma cell stage) was extracted, and virus integration was determined. Averaged provirus copy numbers per cell are shown for untransduced CD34$^+$ cells and CD34$^+$ cells originally transduced by different lentiviral constructs. The results are shown as mean plus SE from combined data obtained from experiments for the same transgene (vector only, GFP, or b12; regardless of U, MH, or EEK promoters). There were 5, 3, 6, and 6 biologic replicates for no virus, vector, GFP, and b12, respectively. The provirus copy numbers per cell at plasma cell stage, on average, were not statistically different from those of their progenitors (P=0.26) under student 2-tailed t test.

Figure 11:
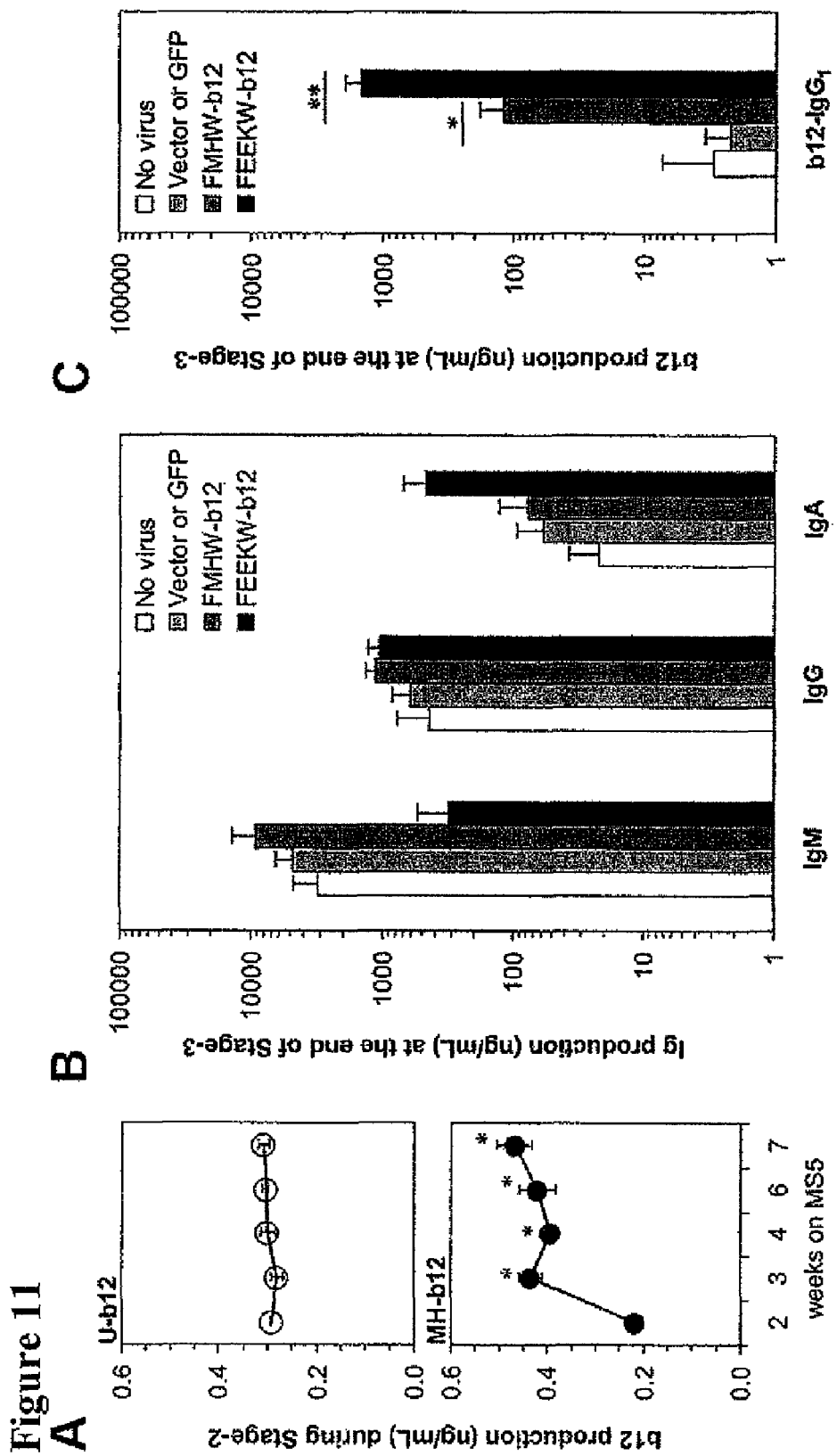
Figure 11:
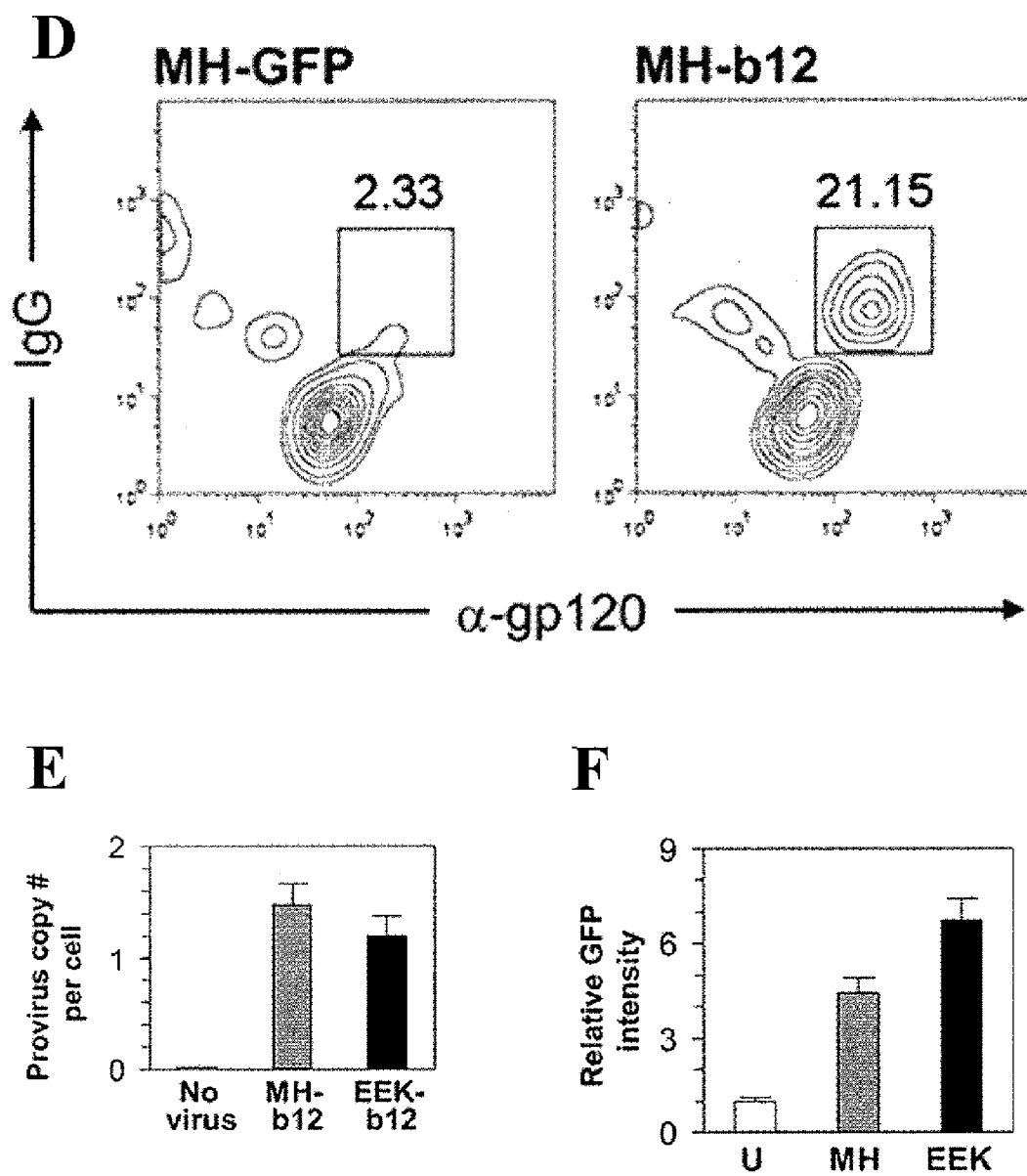
Figure 8:
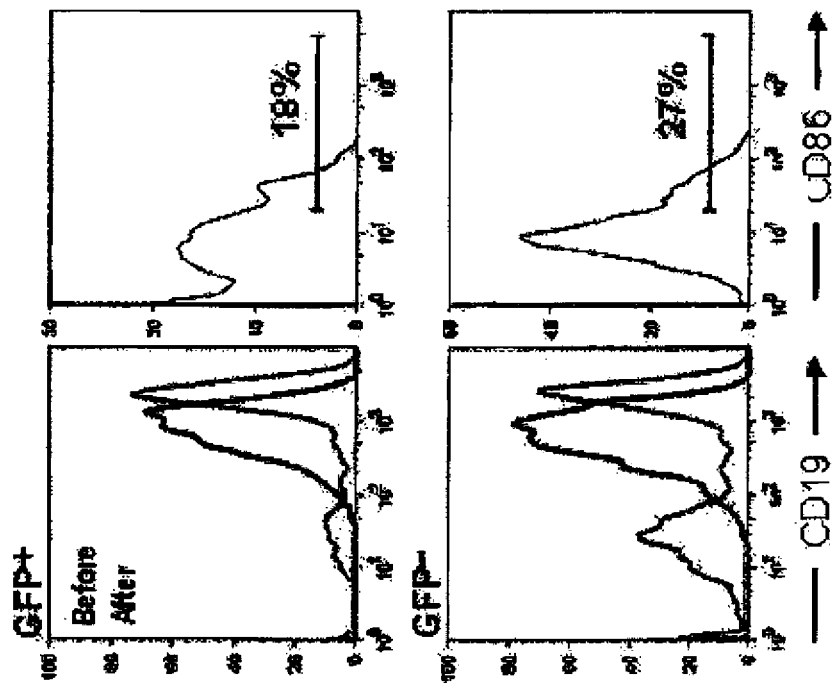
Figure 8:
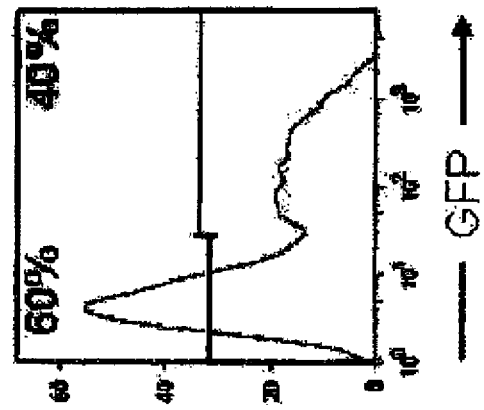

FIG. 11A shows production levels of B12 protein during stage 2. The B12 protein levels were measured using b12-specific ELISA and are shown by weeks. The culture media were changed biweekly, and thus, the data represent the accumulation of the antibody in 3 to 4 days. The results are mean plus or minus SE from 3 independent cultures. * indicates significant difference from week 2 (P<0.05).

FIG. 11B shows Ig production levels at the end of stage 3. A total of 50,000 cells of each treatment from stage 2 were transferred to stage 3 of 500 μL per well. Total IgM, IgG, and IgA levels were measured, and the results are mean plus SE from 3 independent cultures. "Vector or GFP" represents the averaged effect of empty vectors (FMHW and FEEKW) and GFP-containing vectors (MH-GFP and EEK-GFP).

FIG. 11C shows production levels of b12-IgG$_1$ at the end of stage 3 using b12-specific ELISA assay (*P<0.02; **P<0.002). As in FIG. 6B, "Vector or GFP" represents the averaged effect of empty vectors (FMHW and FEEKW) and GFP-containing vectors (MH-GFP and EEK-GFP).

FIG. 11D shows the detection of B12-IgG$_1$ in the cytoplasma of B cells carrying the transgene using intracellular costainings of fluorochrome-labeled gp120$_{MN}$ and anti-IgG interacting with the anti-gp120 epitope and γ heavy chain constant region of b12-IgG$_1$, respectively. MH-GFP- or MH-b12-transduced HSPCs were cultured through stage 2 and stage 3, and surface-stained with anti-CD19 antibody and intracellularly stained with anti-IgG antibody and monomeric gp120. Data were analyzed using flow cytometry and pre-gated on CD19$^+$ cells. Intracellular proteins recognizing gp120 are identified as α-gp120.

FIG. 11E shows the number of provirus copy per cell in cells that were uninfected or infected by MH-b12 or EEK-b12 virus. Genomic DNA from progenitor cells (at week 2 of stage 2) derived from CD34$^+$ cells uninfected or infected by MH-b12 or EEK-b12 virus was extracted and virus integration was determined. Provirus copy numbers per cell are shown as mean plus SE from 3 independent cultures.

FIG. 11F shows the relative GFP intensity in Dakiki plasmacytoma cells that were transduced by U-GFP, MH-GFP, or EEK-GFP lentiviruses. Flow cytometry was performed after 72 hours of incubation and the fold of GFP intensity over the effect of U-GFP (defined as 1) is shown. The difference between MH-GFP and EEK-GFP was significant (P<0.05) under student 2-tailed t tests.

DETAILED DESCRIPTION

Some embodiments of the present application are related to systems, methods and compositions for generating a population of antibody-producing B cells in vitro. A population of antibody-producing B cells can be generated from a population of target cells, preferably a population of hematopoietic stem/progenitor cells (HSPCs). In some embodiments, an in vitro culture system that supports human B-lineage development from HSPCs to antibody-producing B cells, including plasma blasts and/or plasma cells is provided.

In some embodiments, a method for generating a population of antibody-producing B cells in vitro is provided, where the method comprises (a) contacting a population of hematopoietic stem/progenitor cells (HSPCs) in vitro with a polynucleotide delivery system, (b) co-culturing the HSPCs with a population of first supporting cells expressing one or more B-lineage growth factors; (c) co-culturing the CD19$^+$μ$^+$ cells obtained in step (b) with a population of second supporting cells expressing CD40L in the presence of one or more B-cell growth activators. Step (b) may be continued, for example, until at least about 20% of the HSPCs become CD19$^+$μ$^+$, as discussed in more detail below. Step (c) may be continued until, for example, until at least about 20% of the CD19$^+$μ$^+$ cells become B cells that produce the antibody of interest, as discussed in more detail below. In some embodiments, the HSPCs are primary bone marrow cells. In other embodiments, the HSPCs are CD34$^+$ cells from cord blood. It would be appreciated by those skilled in the art that CD34$^+$ cells from cord blood may include both stem cells and progenitor cells that might already committed to lymphoid lineage.

In some embodiments, the method further comprises (d) culturing the HSPCs in the presence of one or more B-cell priming factors for at least about 1 day before step (b). The HSPCs can be cultured in the presence of one or more B-cell priming factors for various numbers of days. For example, the HSPCs can be cultured in the presence of one or more B-cell priming factors for at least about 2 days, at least about 3 days, at least about 4 days, at least about 5 days, at least about 6 days, at least about 7 days, at least about 8 days, at least about 9 days, or at least about 10 days before step (b). In still other embodiments, the HSPCs can be cultured in the presence of one or more B-cell priming factors for about 1 day, about 2 days, about 3 days, about 4 days, about 5 days, about 6 days, about 7 days, about 8 days, about 9 days, or about 10 days before step (b). In yet other embodiments, the HSPCs can be cultured in the presence of one or more B-cell priming factors for about 1 to about 10 days, about 2 to about 9 days, about 2 to about 8 days, about 2 to about 7 days, about 2 to about 6 days, or about 2 to about 5 days before step (b).

Some embodiments provide a method for generating a population of B cells in vitro, comprising: (a) culturing a population of hematopoietic stem/progenitor cells (HSPCs) in the presence of one or more B-cell priming factors for about 2 to about 6 days, (b) co-culturing the HSPCs with a population of first supporting cells expressing one or more B-lineage growth factors; (c) co-culturing the $CD19^+\mu^+$ cells obtained in step (b) with a population of second supporting cells expressing CD40L in the presence of one or more B-cell activators until at least about 20% of the $CD19^+\mu^+$ cells become B cells. Step (b) may be continued, for example, until at least about 20% of the HSPCs become $CD19^+\mu^+$, as discussed in more detail below. In some embodiments, the $CD19^+\mu^+$ cells obtained in step (b) are co-cultured with the population of second supporting cells expressing CD40L in the presence of one or more B-cell activators until at least about 5%, at least about 10%, at least about 15%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the $CD19^+\mu^+$ cells become B cells. In some embodiments, the B cells obtained in step (c) are Ig-secreting B cells.

Various B-cell priming factors can be used in the methods and systems described herein. Examples of B-cell priming factors include, but are not limited to, interleukin 3 (IL-3), Flt3 ligand, thrombopoietin (TPO), stem cell factor (SCF), granulocyte colony-stimulating factor (G-CSF), granulocyte macrophage colony-stimulating factor (GM-CSF), interleukin 7 (IL-7), interleukin (IL-11), anti-phosphatase (Sbfl) and mechano growth factor (MGF). In an embodiment, the HSPCs are cultured in the presence of at least one B-cell priming factor selected from IL-3, Flt3 ligand, TPO, SCF, and G-CSF before step (b). In another embodiment, the HSPCs are cultured in the presence of B-cell priming factors IL-3, Flt3 ligand, TPO, SCF, and G-CSF before step (b). In some embodiments, one or more B-cell priming factors are from humans. In some embodiments, all B-cell priming factors are from humans. In some embodiments, one or more B-cell priming factors are from mammals other than humans. In some embodiments, all B-cell priming factors are from mammals other than humans.

In some embodiments, the first supporting cells are stromal cells. Various stromal cells can be used in the systems and methods described herein. Examples of stromal cell lines include, but are not limited to murine MS5 stromal cell line; murine bone marrow-derived stromal cell lines, such as S10, S17, OP9 and BMS2 cell lines; human marrow stromal cell lines such as those described in U.S. Pat. No. 5,879,940.

In some embodiments, the HSPCs are co-cultured with a population of first supporting cells expressing one or more B-lineage growth factors. In an embodiment, the first supporting cells can express IL-7. In another embodiment, the first supporting cells can express IL-7 and at least one B-lineage growth factor selected from pre-pro-B cell growth-stimulating factor (PPBSF), insulin-like growth factor-1 (IGF-1), interleukin 3 (IL-3), Flt3 ligand, thrombopoietin, stem cell factor (SCF), granulocyte colony-stimulating factor (G-CSF), Granulocyte macrophage colony-stimulating factor (GM-CSF), interleukin 11 (IL-11), anti-phosphatase (Sbfl), and mechano growth factor (MGF). In some embodiments, one or more B-lineage growth factors are from humans. In some embodiments, all B-lineage growth factors are from humans. In some embodiments, one or more B-lineage growth factors are from mammals other than humans. In some embodiments, all B-lineage growth factors are from mammals other than humans.

Many early B-lineage markers are known in the art. For instance, pro-B cells can be identified by CD19 and CD10 co-expression ($CD19^+CD10^+$) and the lack of for expression of surrogate light chains. As pro-B cells differentiate, they develop into $CD19^+\mu^+V_{preB}^+$ pre-B cells and $CD19^+\mu^+ \kappa/\lambda^+$ immature B cells. In some embodiments, the HSPCs are co-cultured with a population of first supporting cells expressing one or more B-lineage growth factors until at least about 20% of the HSPCs become $CD19^+\mu^+$ cells. In other embodiments, the HSPCs are co-cultured with a population of first supporting cells expressing one or more B-lineage growth factors until at least about 5%, at least about 10%, at least about 15%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the HSPCs become $CD19^+\mu^+$. In other embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the $CD19^+\mu^+$ cells obtained in step (b) are $CD19^+\mu^+V_{preB}^+$ pre-B cells and/or $CD19^+\mu^+\kappa/\lambda^+$ immature B cells.

In some embodiments, a B-cell priming factor can also be a B-lineage growth factor. In some embodiments, a B-lineage growth factor can also be a B-cell priming factor.

In some embodiments, the $CD19^+\mu^+$ cells are co-cultured with a population of second supporting cells expressing CD40L in the presence of one or more B cell activators. In an embodiment, the second supporting cells are stromal cells. Various B-cell activators can be used in the methods and systems disclosed herein. Examples of B-cell activators include, but are not limited to, CpG DNA, IL-2, IL-10, IL-15, IL-6, IFN-α, and anti-CD40L. In an embodiment, the B cell activator is CpG DNA. In other embodiment, the B-cell growth factors are CpG DNA, IL-2 and IL-10. in still another embodiment, the B-cell growth factors are CpG DNA and at least one B-cell activator selected from IL-2, IL-10, IL-15, IL-6, IFN-α, and anti-CD40L. In some embodiments, one or more B-cell activators are from humans. In some embodiments, all B-cell activators are from humans. In some embodiments, one or more B-cell activators are from mammals other than humans. In some embodiments, all B-cell activators are from mammals other than humans.

In some embodiments, the CD19$^+$ cells obtained in step (b) is co-cultured with a population of second supporting cells expressing CD40L in the presence of one or more B-cell growth activator until at least about 20% of the CD19$^+$ cells become B cells that produce the antibody of interest. In other embodiments, the CD19$^+$ cells obtained in step (b) is co-cultured with a population of second supporting cells expressing CD40L in the presence of one or more B-cell growth activators until at least about 30% of the CD19$^+$ cells become B cells that produce the antibody of interest. In still other embodiments, the CD19$^+$ cells obtained in step (b) is co-cultured with the population of second supporting cells until at least about 5%, at least about 10%, at least about 15%, at least about 25%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the CD19$^+$ cells become B cells that produce the antibody of interest. In an embodiment, the B cells that produce the antibody of interest are antibody-secreting plasmablasts and plasma cells.

In other embodiments, a method for generating antibody-producing B cells from a population of target cells in vitro is provided, where the method comprises: (a) contacting a population of target cells in vitro with a polynucleotide delivery system, where the polynucleotide delivery system comprises a polynucleotide encoding an antibody of interest; (b) co-culturing the target cells with a population of first supporting cells expressing one or more B-lineage growth factors until at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the target cells become CD19$^+\mu^+$V$_{preB}^+$ or CD19$^+\mu^+\kappa/\lambda^+$; (c) co-culturing the CD19$^+\mu^+$V$_{preB}^+$ and CD19$^+\mu^+\kappa/\lambda^+$ cells obtained in step (b) with a population of second supporting cells expressing CD40L in the presence of one or more B-cell activators until at least 20% of the CD19$^+\mu^+$V$_{preB}^+$ and CD19$^+\mu^+\kappa/\lambda^+$ cells become antibody-producing B cells. In a preferred embodiment, the target cells are mammalian stem cells, including, without limitation, heterogeneous populations of cells that comprise stem cells. The stem cells can be, for example, hematopoietic stem cells. In another embodiment, the target cells are primary bone marrow cells. In still another embodiment, the target cells are CD34$^+$ cells. In yet sill another embodiment, the target cells are CD34$^+$ cells from cord blood. In yet still another embodiment, at most about 75%, at most about 70%, at most about 65%, at most about 60%, at most about 55%, at most about 50%, at most about 45%, at most about 40%, at most about 35%, at most about 30%, at most about 25%, at most about 20%, at most about 15%, at most about 10%, or at most about 5% of the population of target cells are pro-B, pre-B and/or immature B cells. In another embodiment, of the population of target cells are pre-B and immature B cells.

In some embodiments, a method for generating a population of antibody-producing B cells in vitro is provided, where the method comprises (a) contacting a population of target cells in vitro with a polynucleotide delivery system, where the polynucleotide delivery system comprises a polynucleotide encoding an antibody of interest, (b) co-culturing the target cells with a population of first supporting cells expressing one or more B-lineage growth factors until at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the target cells become CD19$^+\mu^+$; (c) co-culturing the CD19$^+\mu^+$ cells obtained in step (b) with a population of second supporting cells expressing CD40L in the presence of one or more B-cell growth activators until at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the CD19$^+\mu^+$ cells become B cells that produce the antibody of interest. In some embodiments, the method further comprises (d) culturing the target cells in the presence of one or more B-cell priming factors for at least about 1 day, at least about 2 days, at least about 3 days, at least about 4 days, at least about 5 days, at least about 6 days, or at least about 7 days before step (b). In some embodiments, the target cells are hematopoietic stem/progenitor cells (HSPCs). In other embodiments, the target cells are hematopoietic stem cells.

In some embodiments, the target cells are pro-B, pre-B and/or immature B cells, and the target cells are co-cultured with the population of first supporting cells expressing one or more B-lineage growth factors until at least about 20% of the target cells become CD19$^+\mu^+$V$_{preB}^+$ and/or CD19$^+\mu^+\kappa/\lambda^+$. In other embodiments, the target cells can be pro-B, pre-B and/or immature B cells and the target cells are co-cultured with the population of first supporting cells expressing one or more B-lineage growth factors until at least about 5%, at least about 10%, at least about 15%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the target cells become CD19$^+$ $\mu^+$V$_{preB}^+$ and/or CD19$^+\mu^+\kappa/\lambda^+$. In some embodiments, the CD19$^+\mu^+$V$_{preB}^+$ and/or CD19$^+\mu^+\kappa/\lambda^+$ cells obtained in step (b) are co-cultured with a population of second supporting cells expressing CD40L in the presence of one or more B-cell growth activators until at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the CD19$^+\mu^+$V$_{preB}^+$ and/or CD19$^+\mu^+\kappa/\lambda^+$ cells become B cells that produce the antibody of interest.

In some embodiments, the method for generating a population of antibody-producing B cells in vitro comprises step (a) contacting a population of target cells in vitro with a polynucleotide delivery system that include a polynucleotide encoding an antibody of interest. In an embodiment, the target cells are hematopoietic stem/progenitor cells (HSPCs). In another embodiment, the target cells are hematopoietic stem cells. In still another embodiment, the target cells are pro-B cells. In yet another embodiment, the target cells are pre-B and/or immature B cells. In yet still another embodiment, the target cells are naïve B cells. In yet still another embodiment, the target cells are activated B cells, plasmablast cells, or plasma cells. In some embodiments, step (a) comprises transfecting the population of target cells with a viral or non-viral vector that comprises a polynucleotide encoding the antibody of interest. In some embodiments, the vector is a retroviral vector. In some embodiments, the retroviral vector is a lentiviral vector.

In some embodiments, the method for generating a population of antibody-producing B cells in vitro comprises step (b) co-culturing the target cells with a population of first supporting cells expressing one or more B-lineage growth factors until at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the target cells become $CD19^+\mu^+$. In some embodiments, the target cells are cells that have been contacted with a polynucleotide delivery system that includes a polynucleotide encoding an antibody of interest. In some embodiment, the target cells are cells that have been transfected with a retroviral vector that includes a polynucleotide encoding the antibody of interest. In some embodiments, the target cells are the cells that have not been contacted with any polynucleotide delivery system. In some embodiments, the target cells are hematopoietic stem/progenitor cells (HSPCs). In other embodiments, the target cells are hematopoietic stem cells. In still other embodiments, the target cells are pro-B cells. In yet other embodiments, the target cells are pre-B and/or immature B cells. In yet still other embodiments, the target cells are naïve B cells. In yet still other embodiments, the target cells are activated B cells, plasmablast cells, and/or plasma cells. In some embodiments, the target cells are co-cultured with the population of first supporting cells until at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the target cells become $CD19^+\mu^+V_{preB}^+$ and/or $CD19^+\mu^+\kappa/\lambda^+$. In yet still other embodiments, the target cells are activated B cells, plasmablast cells, and/or plasma cells. In some embodiments, the target cells are co-cultured with the population of first supporting cells until at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the target cells become $CD19^+\mu^+\delta^+$.

In some embodiments, the method for generating a population of antibody-producing B cells in vitro comprises step (c) co-culturing target cells with a population of second supporting cells expressing CD40L in the presence of one or more B-cell growth activators until at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the target cells become B cells that produce the antibody of interest. In some embodiments, the target cells are $CD19^+\mu^+$ cells, for example, the $CD19^+\mu^+$ cells obtained in step (b). In other embodiments, the target cells are $CD19^+\mu^+V_{preB}^+$ and/or $CD19^+\mu^+\kappa/\lambda^+$ cells, for example, the $CD19^+\mu^+V_{preB}^+$ and/or $CD19^+\mu^+\kappa/\lambda^+$ cells obtained in step (b). In still other embodiments, the target cells are $CD19^+\mu^+\delta^+$ cells, for example, the $CD19^+\mu^+\delta^+$ cells obtained in step (b). In some embodiments, the target cells are pro-B cells. In other embodiments, the target cells are pre-B and/or immature B cells. In still other embodiments, the target cells are naïve B cells.

In some embodiments, the method for generating a population of antibody-producing B cells in vitro comprises step (d) culturing the target cells in the presence of one or more B-cell priming factors before step (b). The target cells can be cultured in the presence of one or more B-cell priming factors for various numbers of days. For example, the target cells can be cultured in the presence of one or more B-cell priming factors for at least about 2 days, at least about 3 days, at least about 4 days, at least about 5 days, at least about 6 days, at least about 7 days, at least about 8 days, at least about 9 days, or at least about 10 days before step (b). In still other embodiments, the target cells can be cultured in the presence of one or more B-cell priming factors for about 1 day, about 2 days, about 3 days, about 4 days, about 5 days, about 6 days, about 7 days, about 8 days, about 9 days, or about 10 days before step (b). In yet other embodiments, the target cells can be cultured in the presence of one or more B-cell priming factors for about 1 to about 10 days, about 2 to about 9 days, about 2 to about 8 days, about 2 to about 7 days, about 2 to about 6 days, or about 2 to about 5 days before step (b). In some embodiments, the target cells are cells that have been contacted with a polynucleotide delivery system that includes a polynucleotide encoding an antibody of interest, for example, the contacted target cells that are produced in step (a). In other embodiments, the target cells are cells that have been transduced with a retroviral vector that includes a polynucleotide encoding the antibody of interest, for example, the transduced target cells that are produced in step (a). In some embodiments, the target cells are the cells that have not been contacted with any polynucleotide delivery system. In some embodiments, the target cells are hematopoietic stem/progenitor cells (HSPCs). In other embodiments, the target cells are hematopoietic stem cells. In still other embodiments, the target cells are pro-B cells. In yet other embodiments, the target cells are pre-B and/or immature B cells.

In some embodiments, the method for generating a population of antibody-producing B cells in vitro does not comprise step (a) contacting a population of target cells in vitro with a polynucleotide delivery system that include a polynucleotide encoding an antibody of interest. In other embodiments, the method for generating a population of antibody-producing B cells in vitro does not comprise step (b) co-culturing the target cells with a population of first supporting cells expressing one or more B-lineage growth factors. In still other embodiments, the method for generating a population of antibody-producing B cells in vitro does not comprise step (c) co-culturing target cells with a population of second supporting cells expressing CD40L in the presence of one or more B-cell growth activators. In yet other embodiments, the method for generating a population of antibody-producing B cells in vitro does not comprise step (d) culturing the target cells in the presence of one or more B-cell priming factors. In yet still other embodiments, the method for generating a population of antibody-producing B cells in vitro comprises steps (a), (b) and (c), but not step (d). In other embodiments, the method for generating a population of antibody-producing B cells in vitro comprises steps (a), (b) and (c), but not step (d). In still other embodiments, the method for generating a population of antibody-producing B cells in vitro comprises steps (a) and (c), but not steps (b) and (d). In still other embodiments, the method for generating a population of antibody-producing B cells in vitro comprises steps (b) and (c), but not steps (a) and (d).

In some embodiments, step (a) contacting a population of target cells in vitro with a polynucleotide delivery system that include a polynucleotide encoding an antibody of interest is performed after step (d) culturing the target cells in the presence of one or more B-cell priming factors and/or step (b) co-culturing the target cells with a population of first supporting cells expressing one or more B-lineage growth factors.

A. DEFINITIONS

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989). Any methods, devices and materials similar or equivalent to those described herein can be used in the practice of embodiments disclosed herein.

As used herein, the term "polypeptide" refers to a polymer of amino acids. A polypeptide can be of various lengths. Thus, peptides, oligopeptides, and proteins are included within the definition of polypeptide. A polypeptide can be with or without N-terminal methionine residues. A polypeptide may include post-translational modifications, for example, glycosylations, acetylations, phosphorylations and the like. Examples of "polypeptide" include, but are not limited to, polypeptides containing one or more analogs of an amino acid (including, for example, unnatural amino acids, non-coded amino acids, etc.), polypeptides with substituted linkages, fusion proteins, as well as polypeptides with other modifications known in the art, both naturally occurring and non-naturally occurring.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

As used herein, an "antigen" is any molecule that is capable of binding to an antigen specific polypeptide. Preferred antigens are capable of initiating an immune response upon binding to an antigen specific polypeptide that is expressed in an immune cell. In some embodiments, an antigen is associated with a disease or disorder of interest. The antigen is not limited in any way and is preferably chosen based on the desired immune response. Antigens may be, for example, polypeptides, carbohydrates, lipids or nucleic acids.

Examples of antigens to which an immune response can be developed include, without limitation, tumor antigens, viral antigens, microbial antigens, allergens, and autoantigens. In an embodiment, the antigen is a viral antigen, such as an HIV antigen. In another embodiment, the antigen is a tumor associated antigen (TAA).

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas.

"Native antibodies" and "native immunoglobulins" are usually heterotetrameric glycoproteins, composed of two identical light (L) chains and two identical heavy (H) chains. Each light chain is linked to a heavy chain by a disulfide bond. The number of disulfide linkages varies among the heavy chains of different immunoglobulin isotypes. Each heavy chain comprises a variable domain ($V_H$) followed by a number of constant domains. Each light chain comprises a variable domain at one end ($V_L$) and a constant domain at its other end. The constant domain of the light chain is aligned with the first constant domain of the heavy chain, and the light-chain variable domain is aligned with the variable domain of the heavy chain.

The term "antibody" herein is used in the broadest sense and specifically covers human, non-human (e.g. murine) and humanized monoclonal antibodies (including full length monoclonal antibodies), polyclonal antibodies, multi-specific antibodies (e.g., bispecific antibodies), and antibody fragments so long as they exhibit the desired biological activity. Various antibodies can be expressed in the system and method disclosed herein. In some embodiments, the antibody is b12, a human monoclonal neutralizing antibody that neutralizes many primary isolates of different genetic subtypes of HIV-1.

The term "target cells" used herein refers to any cells that are capable of differentiating into an antibody-producing B cell, including, without limitation, an activated B cell, a plasmablast, and a plasma cells. Target cells include, but are not limited to, stem cells, particularly hematopoietic stem cells; and lymphoid progenitor cells.

The term "mammal" is defined as an individual belonging to the class Mammalia and includes, without limitation, humans, domestic and farm animals, and zoo, sports, or pet animals, such as sheep, dogs, horses, cats or cows. Preferably, the mammal herein is human.

As used herein, the term "B-cell priming factor" refers to any compounds that are capable of supporting or promoting the commitment of hematopoietic stem cells and/or lymphoid progenitor cells to B-lineage development. A compound can be a small molecule, a polypeptide, a protein, or a nucleic acid. Various B-cell priming factors can be used in the methods and systems described herein. Examples of B-cell priming factors include, but are not limited to, interleukin 3 (IL-3), Flt3 ligand, thrombopoietin, stem cell factor (SCF), granulocyte colony-stimulating factor (G-CSF), granulocyte macrophage colony-stimulating factor (GM-CSF), interleukin 7 (IL-7), interleukin 11 (IL-11), anti-phosphatase (Sbfl), and mechano growth factor (MGF). One of skill in the art will be able to select the amount of a B-cell priming factor to use based on the particular circumstances. Generally, from about 1 to about 1000 ng/ml of a B-cell priming factor can be used in the methods or systems described herein; however, in the typical situation from about 1 to about 100 ng/ml of a B-cell priming factor can be used. However, in some situations, more or less amount of a B-cell priming factor may be used. In situations where more than one B-cell priming factor is used, the amount of each B-cell priming factor may the same, or the amount of each B-cell priming factor may be different from each other.

As used herein, the term "B-lineage growth factor" refers to any compounds that are capable of promoting one or more stages of B cell differentiation during B-lineage development. B-lineage growth factors can be small molecules, polypeptides, proteins, or nucleic acids. Non-limiting examples of the stages in B-lineage development include: the stage from progenitor B cells to early pro-B cells, the stage from early pro-B cells to late pro-B cells, the stage from late pro-B cells to large pre-B cells, the stage from large pre-B cells to small pre-B cells, the stage from small pre-B cells to immature B cells, and the stage from immature B cells to mature B cells. Examples of B-lineage growth factor include, but are not limited to, interleukin 7 (IL-7), pre-pro-B cell growth-stimulating factor (PPBSF), insulin-like growth factor-1 (IGF-1), interleukin 3 (IL-3), Flt3 ligand, thrombopoietin, stem cell factor (SCF), granulocyte colony-stimulating factor (G-CSF), granulocyte macrophage colony-stimulating factor (GM-CSF), interleukin 11 (IL-11), anti-phosphatase (Sbfl), and mechano growth factor (MGF). One of skill in the art will be able to select the amount of a B-lineage growth factor based on the particular circumstances. Generally, from about 1 to about 1000 ng/ml of a B-lineage growth factor can be used in the methods or systems described herein. However, in the typical situation from about 1 to about 300 ng/ml, about 20 to about 200 ng/ml, about 50 to about 150 ng/ml, about 80 to about 150 ng/ml of a cytokine B-cell activator can be used. However, in some situations, more or less amount of a B-lineage growth factor may be used. In situations where more than one B-lineage growth factor is used, the amount of each B-lineage growth factor may the same, or the amount of each B-lineage growth factor may be different from each other.

As used herein, the term "B-cell activator" refers to any compounds that are capable of promoting the activation of naïve B cells, preferably the antigen-independent activation of naïve B cells. B-cell activators can be small molecules, polypeptides, proteins or nucleic acids. Conventional methods can be used to determine if a compound has the ability of stimulating antigen-independent activation of naïve B cell. For example, the compound can be tested for the activation of naïve B cells isolated from human peripheral blood. Non-limiting examples of B-cell activators include CpG DNA; cytokines, such as IL-2, IL-3, IL-4, IL-6, IL-10, IL-15, IFNα; anti-CD40L; and lactic acid. One of skill in the art will be able to select the amount of a B-cell activator based on the particular circumstances. Generally, from about 1 to about 1000 ng/ml of a cytokine B-cell activator can be used in the methods or systems described herein; however, in the typical situation from about 1 to about 150 ng/ml, or about 1 to about 100 ng/ml of a cytokine B-cell activator can be used. However, in some situations, more or less amount may be used. Generally, from about 0.1 to about 5 µM CpG DNA can be used; however, in the typical situation from about 0.5 to about 4 µM, or about 1 to about 3.5 µM, or about 1.5 to about 3 µM, or about 2 to about 2.5 µM CpG DNA can be used. In situations where more than one B-cell activator is used, the amount of each B-cell activator may the same, or the amount of each B-cell activator may be different from each other.

As used herein, the term "supporting cell" refers to any cells that are capable of creating, promoting, or supporting a microenvironment for the growth, proliferation, differentiation, or expansion of HSPCs or B cells. Suitable supporting cells that can be used in the systems and methods disclosed herein include, but are not limited to, stromal cells and fibroblast cells.

A "vector" is a nucleic acid molecule that is capable of transporting another nucleic acid. Vectors may be, for example, viruses, plasmids, cosmids or phage. An "expression vector" is a vector that is capable of directing the expression of a protein encoded by one or more genes carried by the vector when it is present in the appropriate environment. Vectors are preferably capable of autonomous replication.

The term "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells may include, without limitation, promoters, enhancers, splicing signals and polyadenylation signals.

As used herein, the term "operably linked" is used to describe the connection between regulatory elements and a gene or its coding region. That is, gene expression is typically placed under the control of certain regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element.

As used herein, the term "B cell-specific promoter" refers to any promoter/enhancer sequences that are capable of directing specific transgene expression in B cells. For example, a B cell-specific promoter may be capable of directing transgene expression in plasmablasts and/or plasma cells. Another non-limiting example of a preferred B cell-specific promoter is a promoter capable of directing transgene expression throughout B-cell development from hematopoietic cells in primary and secondary lymphoid organs. A B cell-specific promoter is preferably capable of driving transgene expression without affecting B-cell development. It is not intended that the methods or systems disclosed herein be limited by the source of the B cell-specific promoter. A B cell-specific promoters may be the promoter/enhancer sequence of any B-cell specific genes, and/or variants or engineered portions thereof, that normally controls the expression of genes expressed in a B-cell, examples of which include, but are not limited to, promoters/enhancers of CD19, CD20, CD21, CD22, CD23, CD24, CD40, CD72, Blimp-1, CD79b (also known as B29 or Ig beta), mb-1 (also known as Ig alpha), tyrosine kinase blk, VpreB, immunoglobulin heavy chain, immunoglobulin kappa light chain, immunoglobulin lambda-light chain, immunoglobulin J-chain, etc. Other nonlimiting examples of B cell-specific promoter include synthetic promoters, such as MH promoter and the EEK promoter. As described in details in FIG. 1B and Examples below, the MH promoter contains the human µ heavy chain promoter (VHp) preceded by the iEµ enhancer flanked by matrix association regions (MAR), and the EEK promoter contains the human κ light chain promoter (VKp) preceded by an intronic enhancer (iEκ), a MAR, and a 3' enhancers (3'Eκ).

The term "transfection" refers to the introduction of a nucleic acid into a host cell by nucleic acid-mediated gene transfer, such as by contacting the cell with a polynucleotide delivery system as described below.

"Transformation," as defined herein, describes a process by which exogenous DNA enters a target cell. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. "Transformed" cells include stably transformed cells in which the inserted DNA is capable of replication either as an autonomously replicating plasmid or as part of the host chromosome. Also included are cells that transiently express the antigen specific polypeptide.

The term "transgene" refers to any nucleotide or DNA sequence that is integrated into one or more chromosomes of a target cell by human intervention. In an embodiment, the transgene comprises a polynucleotide that encodes an antibody of interest. The antibody-encoding polynucleotide is generally operatively linked to other sequences that are useful for obtaining the desired expression of the gene of interest, such as transcriptional regulatory sequences. In another embodiment, the transgene can additionally comprise a DNA sequence that is used to mark the chromosome where it has integrated.

"Retroviruses" are enveloped RNA viruses that are capable of infecting animal cells. "Lentivirus" refers to a genus of retroviruses that are capable of infecting dividing and non-dividing cells. Several examples of lentiviruses include HIV (human immunodeficiency virus; including HIV type 1, and HIV type 2), visna-maedi, the caprine arthritis-encephalitis virus, equine infectious anemia virus, feline immunodeficiency virus (FIV), bovine immune deficiency virus (BIV), and simian immunodeficiency virus (SIV).

"2A sequences" or elements are small peptides introduced as a linker between two proteins, allowing autonomous intraribosomal self-processing of polyproteins (See, for example, de Felipe. Genetic Vaccines and Ther. 2:13 (2004) and deFelipe et al. Traffic 5:616-626 (2004)). These short peptides allow co-expression of multiple proteins from a single vector. Many 2A elements are known in the art. Examples of 2A sequences that can be used in the methods and system disclosed herein, without limitation, include 2A sequences from the foot-and-mouth disease virus (F2A), equine rhinitis A virus (E2A), Thosea asigna virus (T2A), and porcine teschovirus-1 (P2A) as described in U.S. Patent Publication No. 20070116690.

Polynucleotide Delivery System

As used herein, a "polynucleotide delivery system" is any system capable of introducing a polynucleotide, particularly an antibody-encoding polynucleotide into a target cell. Polynucleotide delivery systems include both viral and non-viral delivery systems. One of skill in the art will be able to determine the type of polynucleotide delivery system that can be used to effectively deliver a particular antibody-encoding polynucleotide into a target cell.

The polynucleotide delivery system may be viral. Suitable viral vectors include, but are not limited to, vectors based on RNA viruses, such as retrovirus-derived vectors (for example, Moloney murine leukemia virus (MLV)-derived vectors), and more complex retrovirus-derived vectors (such as Lentivirus-derived vectors); and vectors based on DNA viruses, such as adenovirus-based vectors and adeno-associated virus (AAV)-based vectors. In some embodiments, the polynucleotide delivery system comprises a retroviral vector, more preferably a lentiviral vector. Non-limiting examples of viral vector include lentivirus vectors derived from human immunodeficiency virus 1 (HIV-1), HIV-2, feline immunodeficiency virus (FIV), equine infectious anemia virus, simian immunodeficiency virus (SIV) and maedi/visna virus.

In an embodiment, a modified retrovirus is used to deliver the antibody-encoding polynucleotide to the target cell. The antibody-encoding polynucleotide and any associated genetic elements are thus integrated into the genome of the host cell as a provirus.

Generation of the viral vector can be accomplished using any suitable genetic engineering techniques well known in the art, including, without limitation, the standard techniques of restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)), Coffin et al. (Retroviruses. Cold Spring Harbor Laboratory Press, N.Y. (1997)) and "RNA Viruses: A Practical Approach" (Alan J. Cann, Ed., Oxford University Press, (2000)).

The viral vector may incorporate sequences from the genome of any known organism. The sequences may be incorporated in their native form or may be modified in any way. For example, the sequences may comprise insertions, deletions or substitutions. In a preferred embodiment the viral vector comprises an intact retroviral 5' LTR and a self-inactivating 3' LTR.

In some embodiments, the polynucleotides encoding the heavy chain and the light chain of an antibody of interest (such as the heavy and light variable region of the antibody) can be introduced into the target cell, either as a single polynucleotide in a single polynucleotide delivery system, or as separate polynucleotides in one or more polynucleotide delivery systems. Preferably, a single polynucleotide delivery system is utilized, comprising polynucleotides encoding each chain of the antibody.

For example, when a polynucleotide encoding the heavy chain of an antibody of interest is to be delivered, it is advantageous to also introduce a polynucleotide encoding the light chain of the antibody of interest. If the polynucleotide delivery system has sufficient capacity, the heavy and light chains can be introduced together, for example as a single antibody-encoding polynucleotide. Thus, an embodiment of the polynucleotide delivery system comprises a polynucleotide encoding the heavy chain of the antibody and a polynucleotide encoding the light chain of the antibody. Preferably, one of the chains is preceded by an IRES or 2A element, as discussed below, in order to facilitate equivalent expression of each subunit. Alternatively, polynucleotides encoding the heavy and light chains can be introduced separately into the target cell, each in an appropriate polynucleotide delivery system, for example each as a separate retroviral particle.

Vector

A polynucleotide deliver system may comprise one or more vectors. A vector can comprise the antibody-encoding polynucleotide sequences, optionally associated with one or more regulatory elements that direct the expression of the coding sequences. Eukaryotic cell expression vectors are well known in the art and are available from a number of commercial sources. The choice of vectors and/or expression control sequences to which the antibody-encoding polynucleotide sequence is operably linked depends directly, as is well known in the art, on the functional properties desired, such as protein expression, and the target cell to be transformed. A preferred vector contemplated by the present invention is capable of directing the insertion of the antibody-encoding polynucleotide into the chromosomes of the target cells and the expression of the antibody encoded by the antibody-encoding polynucleotide.

Expression control elements that may be used for regulating the expression of an operably linked antigen-specific polypeptide encoding sequence are known in the art and include, but are not limited to, inducible promoters, constitutive promoters, secretion signals, enhancers and other regulatory elements.

In some embodiments, a vector comprising an antibody-encoding polynucleotide can include a prokaryotic replicon (that is, a DNA sequence having the ability to direct autonomous replication and maintenance of the recombinant DNA molecule extrachromosomally in a prokaryotic host cell), such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

In other embodiments, the vectors used in the polynucleotide delivery system can include a gene for a selectable marker that is effective in a eukaryotic cell, such as a drug resistance selection marker. This gene encodes a factor necessary for the survival or growth of transformed host cells grown in a selective culture medium. Host cells not transformed with the vector containing the selection gene will not survive in the culture medium. Typical selection genes encode proteins that confer resistance to antibiotics or other toxins, e.g., ampicillin, neomycin, methotrexate, or tetracycline, complement auxotrophic deficiencies, or supply critical nutrients withheld from the media. The selectable marker can optionally be present on a separate plasmid and introduced by co-transfection.

Vectors used in the polynucleotide delivery system will usually contain a promoter that is recognized by the target cell and that is operably linked to the antigen-specific polynucleotide. A promoter is an expression control element formed by a DNA sequence that permits binding of RNA polymerase and transcription to occur. Promoters are untranslated sequences that are located upstream (5') to the start codon of a structural gene (generally within about 100 to 1000 bp) and control the transcription and translation of the antigen-specific polynucleotide sequence to which they are operably linked. Promoters may be inducible or constitutive. Inducible promoters initiate increased levels of transcription from DNA under their control in response to some change in culture conditions, such as a change in temperature.

One of skill in the art will be able to select an appropriate promoter based on the specific circumstances. Many different promoters are well known in the art, as are methods for operably linking the promoter to the antibody-encoding polynucleotide. Both native promoter sequences and many heterologous promoters may be used to direct expression of the antigen-specific polypeptide. However, heterologous promoters are preferred, as they generally permit greater transcription and higher yields of the desired protein as compared to the native promoter. The promoter may be obtained, for example, from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). The promoter may also be, for example, a heterologous mammalian promoter, e.g., an immunoglobulin promoter, a B cell-specific promoter (e.g., the MH promoter and the EEK promoter), or the promoter normally associated with the native sequence, provided such promoters are compatible with the target cell.

When the vector comprises two or more sequences from which expression is desired, each additional sequence beyond the first is preferably linked to an element that facilitates co-expression, such as an internal ribosomal entry sequence (IRES) element (U.S. Pat. No. 4,937,190), or a 2A element. For example, IRES or 2A elements are preferably used when a single vector comprises sequences encoding each subunit of a multi-subunit protein. In the case of that the protein of interest is immunoglobulin with a desired specificity, for example, the first coding region (encoding either the heavy or light chain of immunoglobulin) is located downstream from the promoter. The second coding region (encoding the remaining chain of immunoglobulin) is located from the first coding region, and an IRES or 2A element is disposed between the coding regions, preferably immediately preceding the second coding region. The incorporation of an IRES or 2A element between the sequences of a first and second gene (encoding the heavy and light chains, respectively) can allow both chains to be expressed from the same promoter at about the same level in the target cell.

Using the disclosure provided herein, one of skill in the art will recognize that the efficacy of a particular delivery system can be tested by transforming primary bone marrow cells with a vector comprising a gene encoding a reporter protein and measuring the expression using a suitable technique, for example, measuring fluorescence from a green fluorescent protein conjugate. Suitable reporter genes are well known in the art.

Transformation of appropriate cells with vectors of the present application is accomplished by well-known methods, and the method to be used is not limited in any way. A number of non-viral delivery systems are known in the art, including for example, electroporation, lipid-based delivery systems including liposomes, delivery of "naked" DNA, and delivery using polycyclodextrin compounds, such as those described in Schatzlein A G. 2001. Non-Viral Vectors in Cancer Gene Therapy: Principles and Progresses. *Anticancer Drugs*. Cationic lipid or salt treatment methods are typically employed, see, for example, Graham et al., Virol., 1973, 52:456; Wigler et al., Proc. Natl. Acad. Sci. USA, 1979, 76:1373-1376. The calcium phosphate precipitation method is preferred. However, other methods for introducing the vector into cells may also be used, including nuclear microinjection and bacterial protoplast fusion.

A viral vector can be used in the method or system described herein. Recombinant virus produced from the viral vector may be delivered to the target cells in any way that allows the virus to infect the cells. Preferably the virus is allowed to contact the cell membrane, such as by incubating the cells in medium that comprises the virus.

Target Cells

Target cells include both germline cells and cell lines and somatic cells and cell lines. Target cells can be stem cells derived from either origin. When the target cells are germline cells, the target cells are preferably selected from the group consisting of single-cell embryos and embryonic stem cells (ES). When the target cells are somatic cells, the cells include, for example, immature or mature lymphocytes, including, but not limited to, pre-B, pro-B, immature, naive B cells and activated B cells.

A target cell may be a stem cell or stem cell line, including without limitation heterogeneous populations of cells that contain stem cells.

In some embodiments, the target cells are hematopoietic stem/progenitor cells (HSPCs). Preferably, the target cells are hematopoietic stem cells. In an embodiment, the target cells are primary bone marrow cells. In another embodiment, the target cells are CD34+ cells from cord blood.

Target cells can be derived from any mammalian organism including without limitation, humans, pigs, cows, horses, sheep, goats, rats, mice, rabbits, dogs, cats and guinea pigs. Target cells may be obtained by any method known in the art.

Target cells may be contacted with the polynucleotide delivery system either in vivo or in vitro. Preferably, target cells are maintained in culture and are contacted with the polynucleotide delivery system in vitro. Methods for culturing cells are well known in the art.

Diagnostic Applications

As described below, the methods for generating antibody-producing B cells as disclosed herein can produce an antibody of interest useful in detecting a disease or disorder and/or monitoring the progression of a disease or disorder. As used herein, the phrase "diagnostic" refers identifying the presence of or nature of a disease or disorder. The detection of an antigen (for example, an antigen protein, an antigen nucleic acid sequence, an antigen peptide, an antigen lipid, an antigen carbohydrate, and an antigen small molecule) associated with a disease or disorder) provides a means of diagnosing the disease or disorder. Such detection methods may be used, for example, for early diagnosis of the condition, to determine whether a subject is predisposed to a disease or disorder, to monitor the progress of the disease or disorder or the progress of treatment protocols, to assess the severity of the disease or disorder, to forecast the an outcome of a disease or disorder and/or prospects of recovery, or to aid in the determination of a suitable treatment for a subject. The detection can occur in vitro or in vivo.

Diseases contemplated for diagnosis in embodiments described herein include any disease in which an antigen, such as an antigen associated with the disease, can bind specifically to the antibody of interest. For example, the antigen can be a tumor antigen, a viral antigen, a microbial antigen, an allergen, and an autoantigen. In an embodiment, the antigen is a viral antigen, such as an HIV antigen. In another embodiment, the antigen is a tumor associated antigen (TAA).

In some embodiments, the disease to be diagnosed is a type of cancer, such as, for example, leukemia, carcinoma, lymphoma, astrocytoma, sarcoma and particularly Ewing's sarcoma, glioma, retinoblastoma, melanoma, Wilm's tumor, bladder cancer, breast cancer, colon cancer, hepatocellular cancer, pancreatic cancer, prostate cancer, lung cancer, liver cancer, stomach cancer, cervical cancer, testicular cancer, renal cell cancer, and brain cancer.

In other embodiments, the disease to be diagnosed is associated with infection by an intracellular parasite. For example, the intracellular parasite may be a virus such as, for example, an adenovirus, cytomegalovirus, Epstein-Barr virus, herpes simplex virus, human herpesvirus 6, varicella-zoster virus, hepatitis viruses, papilloma virus, parvovirus, polyomavirus, measles virus, rubella virus, human immunodeficiency virus (HIV), or human T cell leukemia virus. In other embodiments, the intracellular parasite may be a bacterium, protozoan, fungus, or a prion. More particularly, the intracellular parasite can be, for example, *Chlamydia, Listeria, Salmonella, Legionella, Brucella, Coxiella, Rickettsia, Mycobacterium, Leishmania, Trypanasoma, Toxoplasma*, and *Plasmodium*.

The antibodies produced by the antibody-producing B cells generated by the methods and systems described herein have a wide variety of utilities. Many other uses for antibodies are well known in the art, including therapeutic, diagnostic, forensic, environmental, and commercial applications. For example, an antigen, either in vitro or in vivo, can bind to an antibody of interest. Thus, methods disclosed herein can be used for detecting the presence of an organisms and/or an antigen (for example, polypeptides, carbohydrates, lipids or nucleic acids), in a forensic/environmental sample or tissues/cells. In some embodiments, the methods can be used in producing antibody that can allow the detection of activated state of an enzyme. In other embodiments, the methods can be used to purifying proteins, e.g., in laboratory or industrial scales.

EXAMPLES

Additional embodiments are disclosed in further detail in the following examples, which are not in any way intended to limit the scope of the claims.

Experimental Methods

The following experimental methods were used for Examples 1-4 described below.

Plasmid Construction

Figure 1:
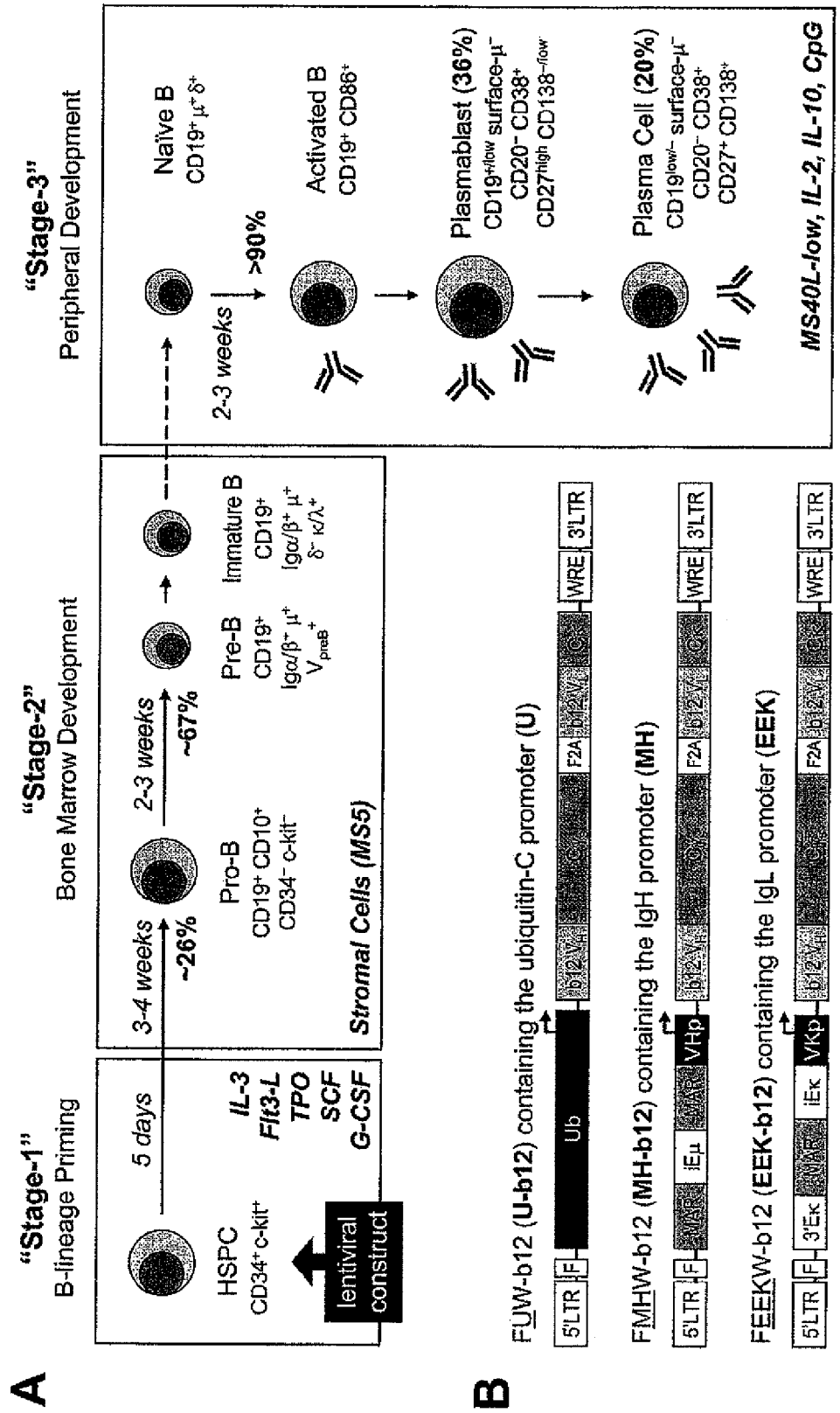
FIG. 1A schematically illustrates an embodiment of the in vitro human B lymphopoiesis culture system. Lentiviral constructs were introduced to the HSPCs to achieve B-cell programming. During the 5 days of stage 1, IL-3 (10 ng/mL), Flt3 ligand (Flt3-L; 10 ng/mL), thrombopoietin (TPO; 10 ng/mL), SCF (5 ng/mL), and G-CSF (5 ng/mL) primed the HSPCs for B-lineage commitment. The 6-week stage 2 used stromal support (MS5) and generated a mixture of pre-B and immature B cells from CD34$^+$ HSPCs. The 3-week stage 3 promoted B-cell activation, proliferation, and differentiation into antibody-secreting plasmablasts and plasma cells in the presence of IL-2 (10 ng/mL), IL-10 (100 ng/mL), CpG (2 μM), and MS5 cells stably expressing a low level of CD40L (MS40L-low cells). The surface markers, such as CD34, CD19, CD10, CD20, CD38, CD27, and CD138, at different stages of B-cell development are shown.
FIG. 1B schematically illustrates three lentiviral constructs (FUW-b12, FMHW-b12 and FEEKW-b12) that carried the secretory form of b12-IgG$_1$. The expression of secretory form of b12-IgG$_1$ was driven, respectively, by the ubiquitin-C promoter in FUW-b12, by the Ig heavy chain promoter in FMHW-b12, and by the Ig light chain promoter in FEEKW-b12. The MH promoter (SEQ ID NO:1) contained the human μ chain promoter (VHp) preceded by the iEμ enhancer flanked by matrix association regions (MAR). The EEK promoter (SEQ ID NO:2) contained the light chain promoter (VKp) preceded by an intronic enhancer (iE$_κ$), an MAR, and a 3' enhancer (3'E$_κ$). The secretory γ (γ$_s$) heavy chain and κ light chain genes with b12 variable regions were linked through F2A sequences. The long terminal repeats (LTR), HIV-1 flap element (F), and woodchuck hepatitis virus post-transcriptional regulatory element (WRE) of the vector are indicated.

The light and heavy chain variable sequences of anti-HIV antibody b12 were amplified and inserted upstream of the human κ chain constant and secretory $IgG_1$ constant regions, respectively. The two resulting genes were linked by a self-cleaving F2A peptide to form a bicistronic unit. The linked genes were then subcloned into the FUW lentiviral vector to create the lentiviral vector FUW-b12 (also referred as "U-b12" herein) that contained the ubiquitin-C promoter (U) (FIG. 1B). Also, the FMHW lentiviral vector was constructed by replacing the ubiquitin-C promoter in FUW with human μ heavy chain promoter (MH promoter), preceded by Eμ enhancer flanked by matrix association regions (MARs). Similarly, the FEEKW vector was constructed by replacing the ubiquitin-C promoter in FUW by human κ light chain promoter (EEK promoter) preceded by enhancers and MARs. The bicistronic unit of b12 was then subcloned into FMHW and FEEKW to create lentiviral vectors FMHW-b12 (also referred as "MH-b12" herein) and FEEKW-b12 (also referred to as "EEK-b12" herein), respectively (FIG. 1B). In addition, green fluorescent protein (GFP) was subcloned into FUW, FMHW and FEEKW to generate lentiviral vectors FUWG (also referred as "U-GFP" herein), FMHWG (also referred as "MH-GFP" herein), and FEEKWG (also referred as "EEK-GFP" herein). All constructs were tested in Nalm-6 (pre-B), Ramos (naive B), Dakiki (plasmacytoma), and Jurkat cell lines before being introduced into human HSPCs.

Lentiviral Transduction

Lentiviruses were generated by transfection of HEK-293T cells through calcium phosphate precipitation. To prepare high-titer viruses, viral supernatant was concentrated by ultracentrifugation for 90 minutes at 50 000×g. Human cord blood CD34+ HSPCs were maintained for less than 24 hours before infection in Iscove's modified Dulbecco medium (IMDM) containing 10% fetal bovine serum and cytokines. The cytokines included human recombinant interleukin-3 (IL-3; 10 ng/mL), Flt3 ligand (10 ng/mL), thrombopoietin (10 ng/mL), stem cell factor (SCF; 5 ng/mL), and granulocyte-colony stimulating factor (G-CSF; 5 ng/mL) and were given every other day during the infection. Two sequential infections of 0.3 to $0.4 \times 10^6$ HSPCs/well by concentrated lentiviral particles at multiplicity of infection of 1000 were carried out in 48-well plates pre-coated with Retronectin at 50 μg/mL. HSPCs were collected 3 days after infection and analyzed by flow cytometry. The infected cells maintained their progenitor phenotype.

Enzyme-Linked Immunosorbent Assays

Total human IgM, IgG and IgA were assayed using commercial enzymelinked immunosorbent assays (ELISA) kits. The ELISA to detect b12-IgG$_1$ was modified from Selvarajah et al., J Virol., 2005, 79:12148-12163. In the assay, plates were coated overnight at 4° C. with monomeric gp120$_{MN}$ at 2 µg/mL in phosphate-buffered saline (PBS). Wells were washed with PBS containing 0.05% Tween-20 (PBS-T) and blocked with 3% bovine serum albumin (BSA) for 1 hour at room temperature. After BSA was aspirated, dilutions of samples and b12 standard in PBS-T containing 1% BSA were added and incubated at 37° C. for 3 hours. The b12 standard medium was obtained by transfecting 293T cells with U-b12, and its concentration was determined by Biacore gp120-binding assay. Wells were washed again, and goat antihuman IgG F(ab')2 conjugated with horseradish peroxidase diluted 1:1000 was added and incubated for 1 hour at 37° C. Plates were developed by the addition of 3,3',5,5'-tetramethylbenzidine solution. The reaction was stopped by adding 2 M H$_2$SO$_4$, and plates were read at 450 nm on a SpectroMax Reader.

Detection of Virus Integration

Provirus copy numbers were determined by a modified Alu-long terminal repeat (LTR) nested-polymerase chain reaction (PCR) protocol. The first round of PCR allowed the amplification of up to 3 kb between an Alu sequence (Alu-fw: 5'-TCCCAGCTACTGGGGAGGCTGAGG-3', SEQ ID NO: 4) and a sequence immediately downstream of 5'-LTR after the virus is integrated (PBS-bw: 5'-GAGTCCTGCGTC-GAGAGAG-3', SEQ ID NO: 5). The second round used SYBR green-based quantitative PCR to detect a 143-bp sequence of the provirus LTR (late-RT-fw: 5'-TGTGTGC-CCGTCTGTTGTGT-3', SEQ ID NO: 6); and late-RT-bw: 5'-GAGTCCTGCGTCGAGAGAGC-3', SEQ ID NO: 7). To establish the standard curve, an integrated gDNA standard was generated by extracting gDNA from a stable THP-1 cell line with integrated FUW that has been maintained for 6 months, and the provirus copy number in the standard gDNA was determined using serial dilutions of linearized FUW plasmid with known numbers of LTR copies. Genomic DNA of a THP-1 line transduced with an irrelevant vector was used as the negative control. β-Globin was used as the loading control. The detection range of this Alu-LTR nested-PCR protocol was 500 to 6×10$^4$ copies per 50 ng gDNA. The correlation between the amount of genomic DNA and the cell number at different stages of B-cell development was determined experimentally.

Example 1

Stage 1: Priming for B-Lineage Commitment and Programming of Human B Cells Through Lentiviral Transduction of HSPCs In this example, CD34$^+$ cord blood cells were transfected with lentiviral constructis in step (a) and primed for about 5 days in step (b) to commit to B-lineage development in the presence of B-cell priming factors such as IL-3, Flt3 ligand, thrombopoietin, SCF, and G-CSF.

Figure 2:
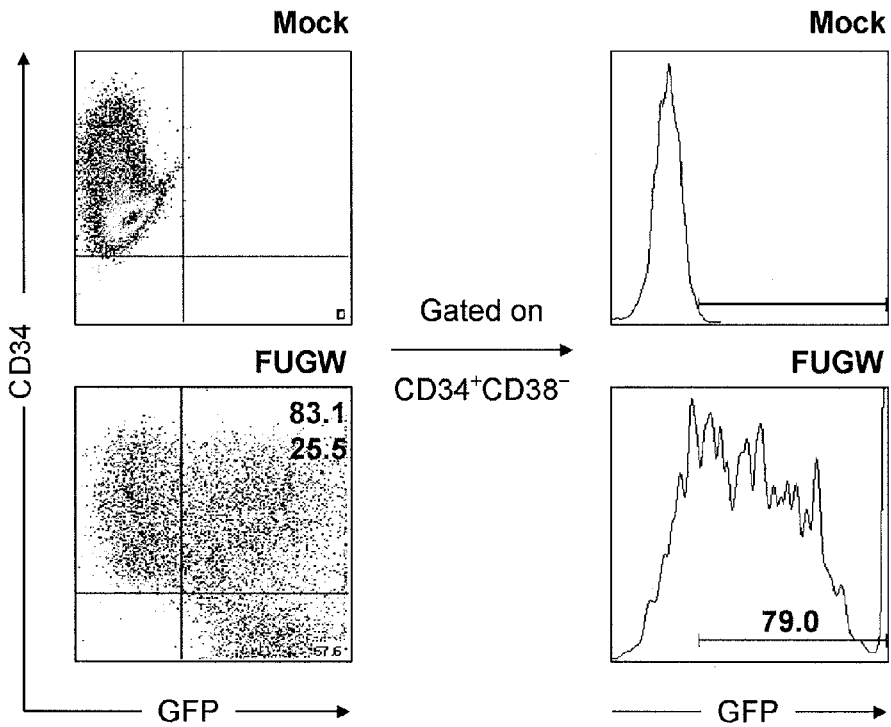
FIG. 2A shows high transduction efficiencies achieved by lentiviral vector FUGW (that is U-GFP). HSPCs were incubated for 24 h in the presence of IL-3 (10 ng/mL), Flt3 ligand (10 ng/mL), thrombopoietin (10 ng/mL), SCF (5 ng/mL) and G-CSF (5 ng/mL). Two sequential infections with mock or FUGW virus at a multiplicity of infection of 1,000 were then given to the HSPCs. The same cytokines were added every other day during the infection. The infected cells were collected 3 days post-infection (a total of 5 days of incubation) and analyzed by flow cytometry.
FIG. 2B shows IgG expression in three cell lines transfected by lentiviral constructs U-b12 or MH-b12. As none of the three cell lines expressed endogenous IgG, the staining of intracellular IgG represented the transgenic b12-IgG$_1$.
FIG. 2C shows the expression and assembly of b12 heavy and light chains in 293T cells transfected with lentiviral vector FUW-b12 under reducing ((+β-mercaptoethanol; or β-ME) and non-reducing conditions (−β-ME). Cellular proteins were extracted and analyzed using SDS-PAGE, followed by Western blotting of IgG-Fc (γ heavy chain/HC) and the κ light chain/LC.
FIG. 2D shows the neutralization ability of b12 antibody produced by 293T cells transfected with lentiviral vector FUW-b12 is comparable to that of purified b12. The culture supernatant was collected and measured by Biacore assay, which gave the concentration of approximately 6 μg/mL of binding to gp120. The concentration of the purified b12 was 125 μg/mL. The culture supernatant and the purified b12 were diluted 5-fold to 1.2 μg/mL and 25 μg/mL of starting concentrations, respectively, when subjected to pseudovirus neutralization assay.
Figure 2:
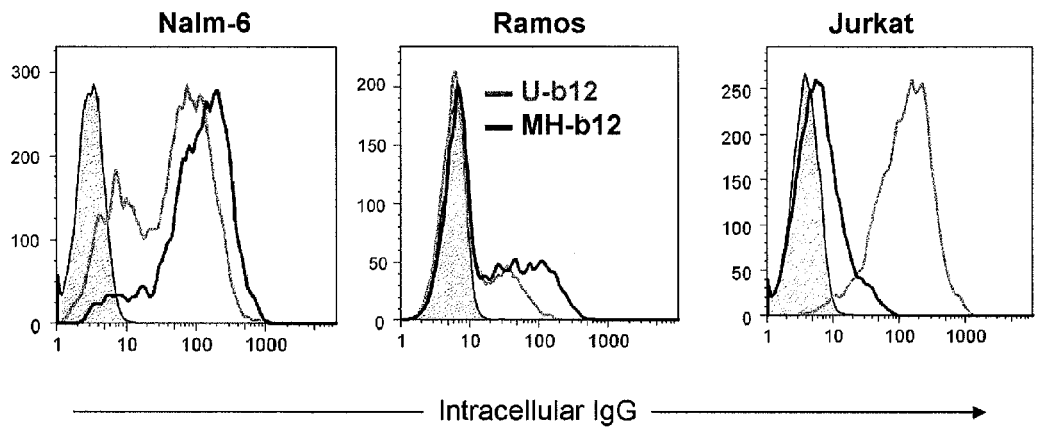
Figure 2:
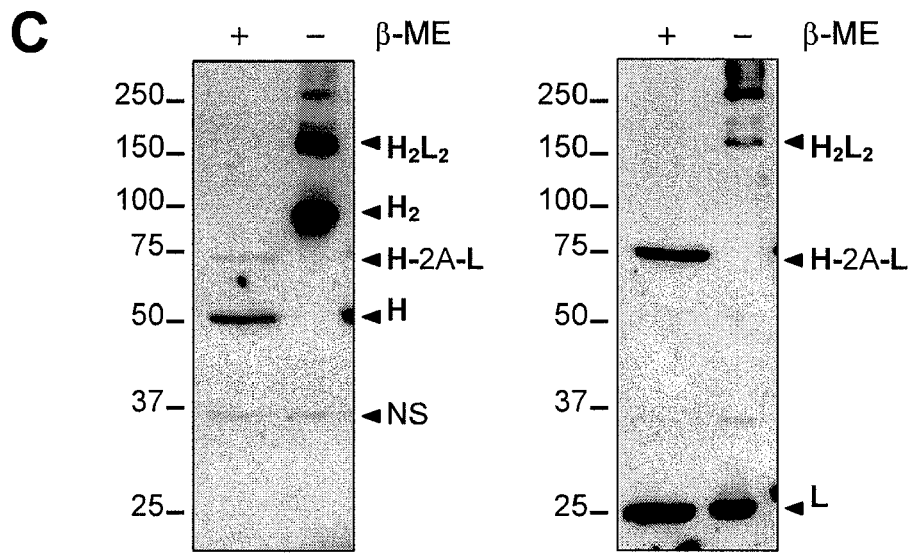
Figure 2:
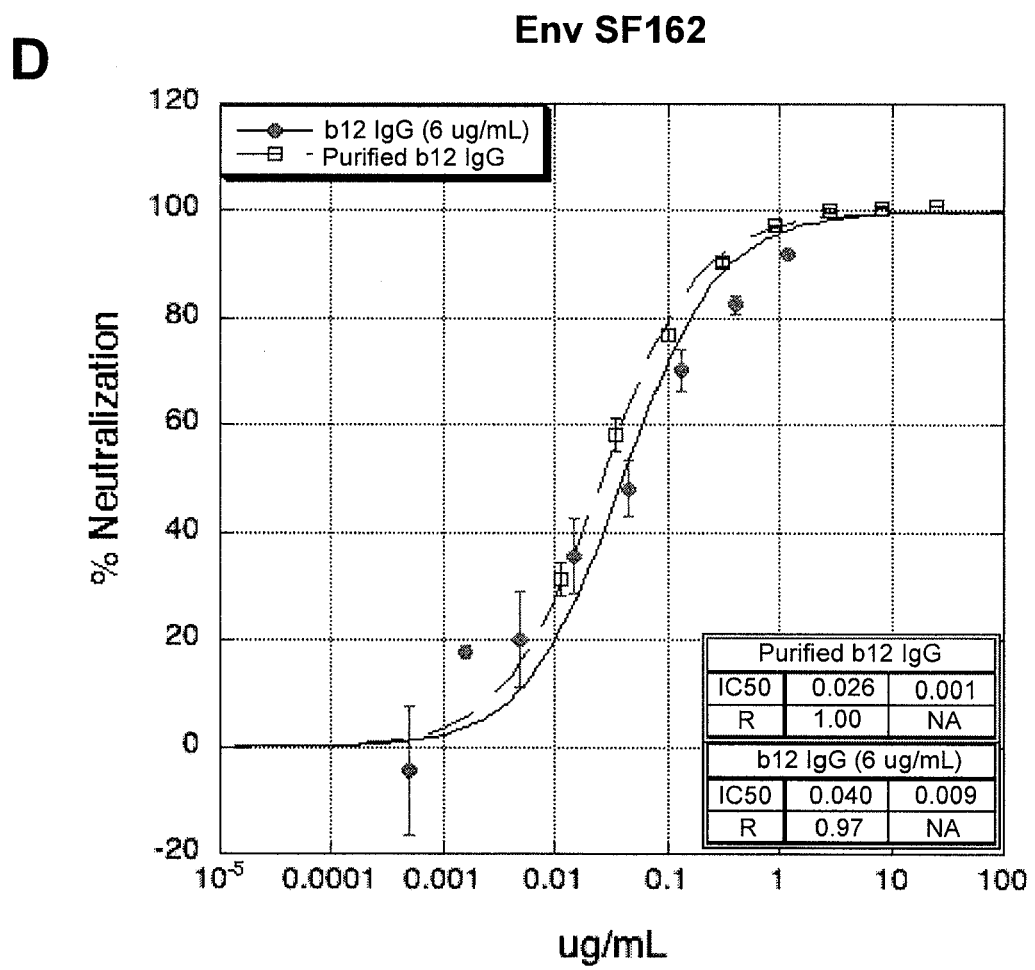

The GFP-encoding lentiviral vector, FUGW, was used to test viral transduction. CD34$^+$ cord blood cells were mixed with Retronectin as a bridge between the virus and the cells. HSPCs were incubated in the presence of a priming mixture of factors that support progenitor cell growth and commitment to the B-cell lineage, including IL-3 (10 ng/mL), Flt3 ligand (10 ng/mL), thrombopoietin (10 ng/mL), SCF (5 ng/mL) and G-CSF (5 ng/mL). Two sequential infections with mock vector or FUGW virus at a multiplicity of infection of 1,000 were then given to the HSPCs. The same mixture of cytokines was added every other day during the infection. The infected cells were collected 3 days post-infection (a total of 5 days of incubation) and analyzed by flow cytometry. As shown in FIG. 2A, a transduction efficiency of more than 80% of CD34$^+$ cells was achieved after 5 days of incubation in the priming mixture of factors. Similar transduction efficiency was observed when gating on CD34$^+$CD38$^-$ cells which were a rare and particularly primitive subpopulation of CD34$^+$ cells in human cord blood.

Lentiviral vectors U-b12, MH-b12, EEK-b12 were transfected into two human B-cell lines (Nalm-6 and Ramos) and one T-cell line (Jurkat) for testing before being used to transduce HSPCs. As none of the three cell lines expressed endogenous IgG, the staining of intracellular IgG represents the transgenic b12-IgG$_1$. The effect of the ubiquitin promoter (U) on b12-IgG$_1$ expression was compared to that of either MH or EEK B cell-specific promoters. As shown in FIG. 2B, the ubiquitin-driven construct U-b12 expressed b12-IgG$_1$ in both B and T-cell lines, whereas MH-b12 which contained the B cell-specific promoter led to strong expression of b12-IgG$_1$ in B cells but little in T cells. Similar effect on b12-IgG$_1$ expression was observed in the case of EEK-b12.

To confirm the functionality of the b12-IgG$_1$ produced by the F2A-containing bicistronic lentivectors, the expression and assembly of b12 heavy and light chains were measured under reducing and non-reducing conditions. 293T cells were transfected with the lentiviral vector FUW-b12. Cellular proteins were extracted and analyzed under reducing (+β-mercaptoethanol; or β-ME) and non-reducing conditions (−β-ME) using SDS-PAGE, followed by Western blotting of IgG-Fc (γ heavy chain/HC) and the κ light chain/LC. More than 90% of heavy (H) and light chains (L) were expressed and cleaved at the F2A site (uncleaved: H-2A-L), most heavy chains formed homodimers (H2; ~100 kD) through disulfide bonds and they picked up the light chains (H2L2) before secretion to the culture medium (FIG. 2C).

Further, the HIV-neutralizing ability of b12-IgG$_1$ was verified using the pseudovirus neutralization assay (FIG. 2D). 293T cells were transfected with the lentiviral vector FUW-b12. The culture supernatant was collected and measured by Biacore assay, which gave the concentration of approximately 6 µg/mL of binding to gp120. The concentration of the purified b12 was 125 µg/mL. The culture supernatant and the purified b12 were diluted 5-fold to 1.2 µg/mL and 25 µg/mL of starting concentrations, respectively, when subjected to pseudovirus neutralization assay. As show in FIG. 2D, the b12-containing culture medium could neutralize the SF162 strain of pseudovirus as potently as the purified b12-IgG$_1$. The neutralizing 50% inhibitory concentrations (IC50's) were 0.040 µg/mL and 0.026 µg/mL for the culture medium and purified b12, respectively.

Example 2

Stage 2: Development of Human B Cells on MS5 Stromal Cells from Primed HSPCs

In this example, murine stromal MS5 cells expressing the B-lineage growth factor IL-7 were used to support the sequential generation of human pro-B, pre-B, and immature B cells from primed HSPCs in step (c). After culturing primed CD34$^+$ HSPCs for 3-4 weeks on MS5 cells, 23-28% of HSPCs became pro-B cells. Furthermore, after an additional 2-3 weeks of incubation, 65-69% of CD19$^+$ cells represented a mixture of pre-B and immature B cells.

MS5 stromal cells were plated at 3×10^4 cells/well in 24-well plates overnight. Then, human HSPCs transduced with lentiviral vectors (U-GFP or MH-GFP) and no-virus control cells were seeded onto the MS5 monolayer respectively at 6×10^4 cells/500 µL per well in Iscove modified Dulbecco medium containing 5% fetal bovine serum. The co-culture of HSPCs and MS5 cells was maintained with biweekly feeding for 5 to 6 weeks, once with the addition of 500 µL of medium and the other time with the removal of 80% of cells after gentle agitation and adding back 300 µL of medium.

Figure 3:
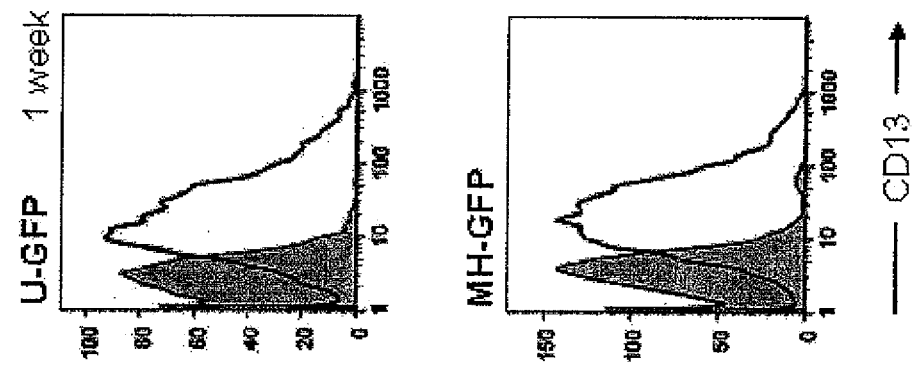
FIG. 3A shows the loss in the expression of progenitor cell markers CD34 and c-kit on HSPCs transduced with lentiviral constructs U-GFP or MH-GFP over time during stage 2.
FIG. 3B shows the appearance of CD13$^+$ myeloid cells at week 1 of stage 2.
Figure 3:
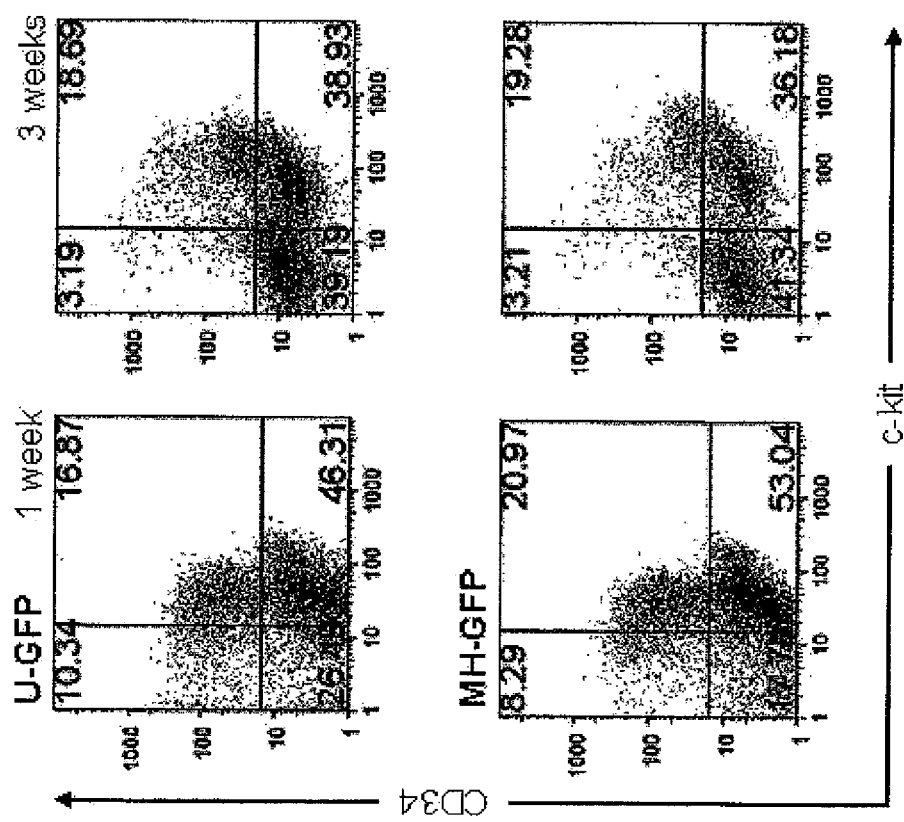
Figure 4:
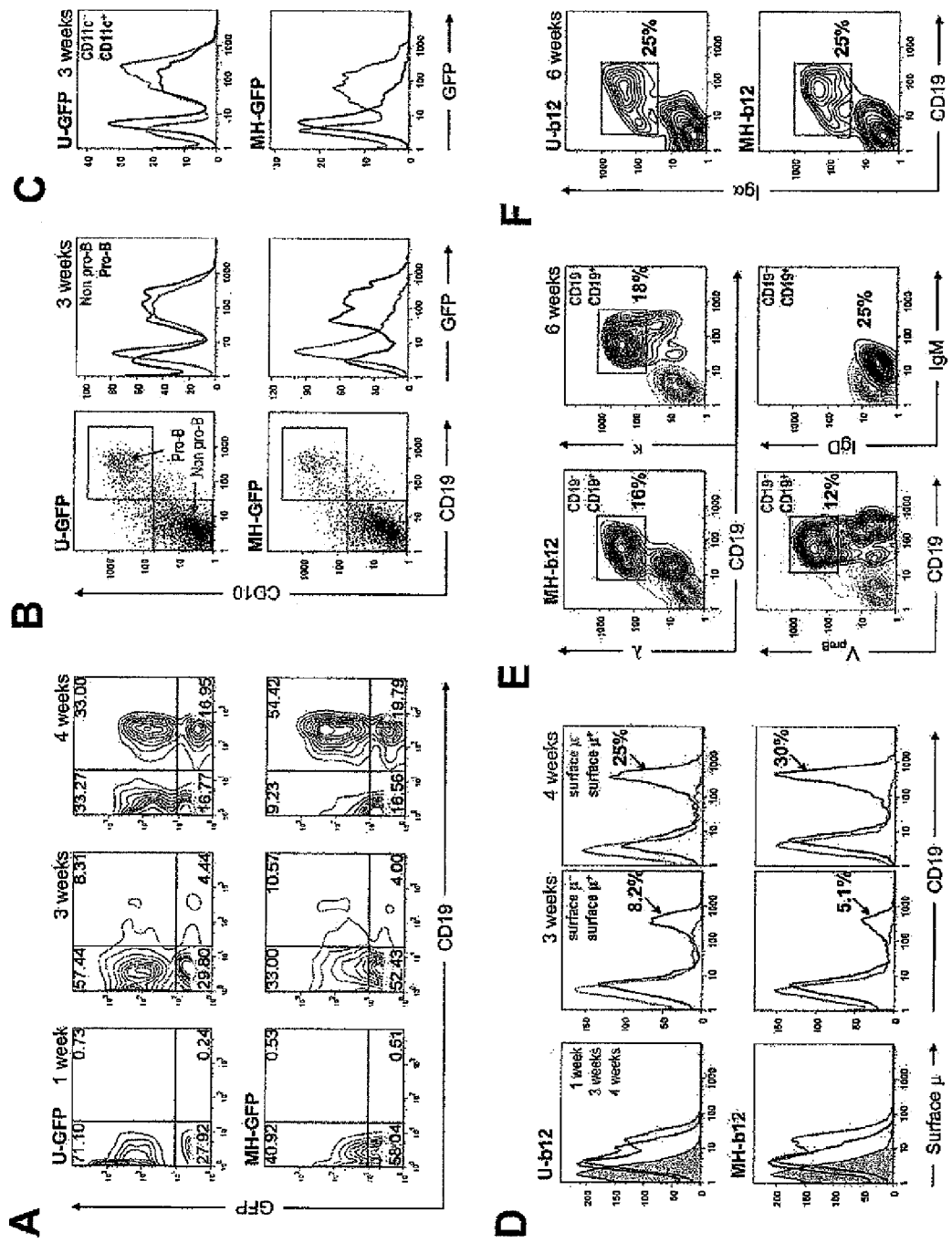
FIG. 4A shows the expression of GFP and CD19 marker in primed HSPCs that have been transduced with either U-GFP (top panels) or MH-GFP (bottom panels) lentiviral constructs. HSPCs primed and transduced with lentiviral constructs were cultured on MS5 stromal cells for the indicated periods of time. GFP expression and appearance of CD19$^+$ cells were monitored using flow cytometry.
FIG. 4B shows pro-B cells started to appear at 3 weeks of stage 2 as monitored by the expression of both CD19 and CD10 on the cell surface. When gates were applied to pro-B versus non-pro-B, and GFP expression was analyzed in these gates, the MH promoter showed pro-B cell-specific expression, whereas the ubiquitin promoter did not discriminate between the cells. The lighter lines represent non-pro-B cells; the darker lines represent pro-B cells.
FIG. 4C shows the comparison between the GFP expression in CD11c$^+$ dendritic cells that were derived from MH-GFP-transduced progenitor cells at 3 weeks into stage 2 and that in CD11c$^-$ cells.
FIG. 4D shows expression levels of surface μ heavy chain and CD19 on cells at different time points (3 weeks (central panels) and 4 weeks (right panels)) of stage 2. The percentages shown are those of total live cells.
FIG. 4E is a plot in which expression levels of λ and κ light chains, V$_{preB}$ surrogate light chain, and μ and δ heavy chains were plotted against CD19 expression at 6 weeks into stage 2, indicating a mixture of pre-B and immature B cells at the end of stage 2. The percentages shown are those of total live cells.
FIG. 4F shows CD19$^+$ cells were positive for Igα at the end of stage 2 (6 weeks). When both Igα and Igβ were examined, the percentage of Igα$^+$ cells and that of Igβ$^+$ cells was similar. In all analyses, cells carrying EEK-b12 showed a similar phenotype to those with MH-b12.

Upon exposure to MS5, the HSPCs lost the expression of CD34 and c-kit, markers for early progenitor cell, and the percentages of double-negative cells (CD34$^-$c-kit$^-$) increased over time (FIG. 3A). No evident differences were observed between the mock-infected CD34$^+$ cells and the CD34$^+$ cells infected with b12-expressing lentiviruses. As shown in FIG. 3B, CD13$^+$ cells representing the myeloid lineage started to appear as early as 1 week after the initiation of co-culture. However, the cooperation of B-cell lineage priming and MS5 stromal support induced the generation of CD19$^+$ early B cells between weeks 3 and 4 (FIG. 4A). After week 4, B cells continued to form and predominated.

Figure 5:
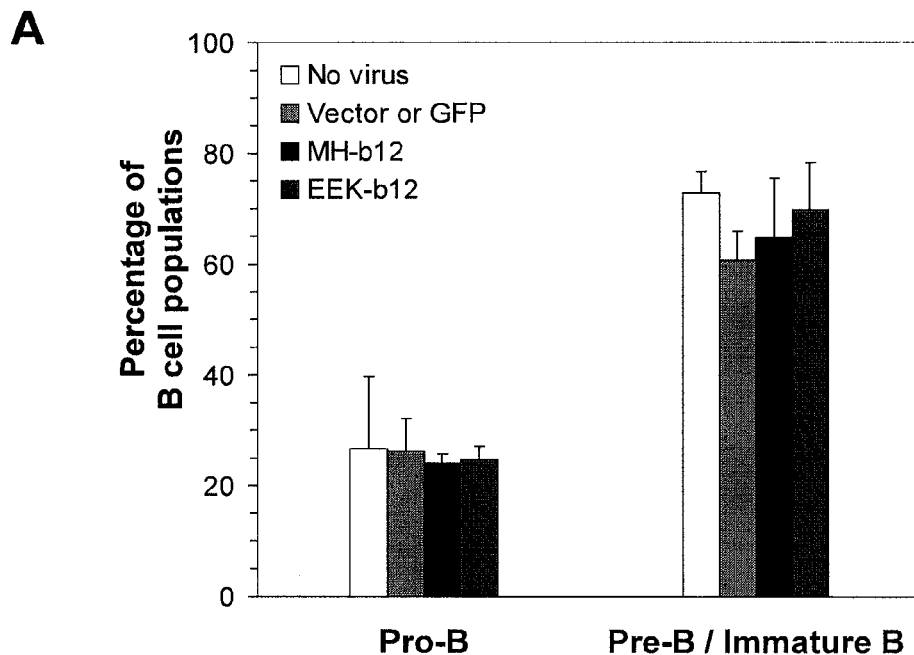
FIG. 5A is a bar graph showing percentages of B cell populations derived from uninfected HSPCs and HSPC transduced with various lentiviral constructs (including empty vectors FMHW and FEEKW; GFP-containing vectors MH-GFP and EEK-GFP; and b12-containing vectors MH-b12 and EEK-b12).
FIG. 5B shows the presence of CD19$^+$CD10$^+$ pre-B and CD19$^+$CD10$^-$ immature B cells in cultures of HSPCs transfected with MH-b12 and EEK-b12 at the end of stage 2 (6 weeks).
Figure 5:
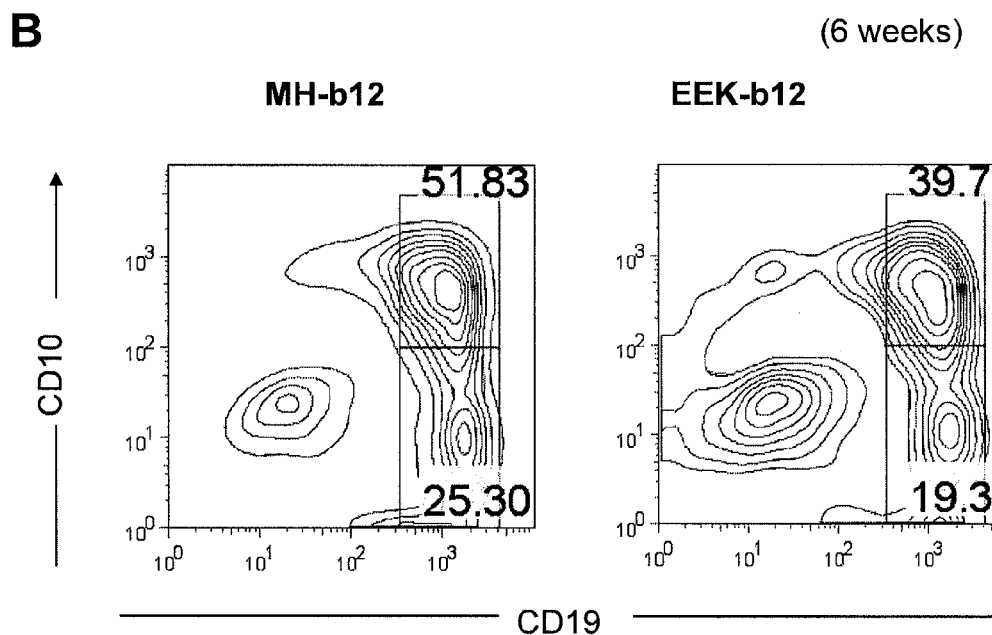

To determine the effect of the transgene on B-cell development during stage 2, uninfected HSPCs (no virus) or HSPCs transduced with different lentiviral constructs were cultured on MS5 stromal cells for 3-4 weeks (representing the stage of pro-B cells) or 6 weeks (representing the time when there is a mixture of pre-B and immature B cells). The results showed that the generation of B cells was not affected by transgene expression (FIG. 5A). Also, although the ubiquitin promoter drove similar levels of GFP expression in both CD19$^-$ and CD19$^+$ cells at 4 weeks, the B cell-specific MH promoter was stronger for expressing GFP in CD19$^+$ cells (FIG. 4A right panels).

At the end of Stage-2 (6 weeks), both CD19$^+$CD10$^+$ pre-B and CD19$^+$CD10$^-$ immature B cells were generated and their proportions were similar regardless of the lentiviral constructs introduced (MH-b12 or EEK-b12). In these particular determinations, the percentage of total CD19$^+$ cells in the case of MH-b12 was higher than that of EEK-b12. See FIG. 5B. However, the averaged effects of lentiviral constructs were the same statistically, as shown in FIG. 5A.

To determine whether stage 2 supported B-cell subpopulations representative of those present in vivo in normal human bone marrow, the surface expression of early B-lineage markers were evaluated. Pro-B cells, identified by CD19 and CD10 co-expression, appeared after 3 weeks (FIG. 4B left panels). These cells were negative for the expression of surrogate light chains, indicating that they were indeed pro-B cells. Also, transgene expression driven by a B cell-specific promoter was found in only pro-B cells but not other cells (FIG. 4B right panels). In contrast, CD11c$^+$ dendritic cells derived from MH-GFP-transduced progenitor cells were negative for GFP (FIG. 4C), consistent with the lack of immunoglobulin transcription in dendritic cells. This indicates that the MH promoter is predominantly active in the B-cell lineage.

After 4 weeks of coculture of transduced cells and MS5 stromal cells, 25% to 30% of total cells were CD19$^+$µ$^+$, up from 5% to 8% at 3 weeks (FIG. 4D). At 6 weeks, CD19$^+$ cell populations consisted of VpreB$^+$ pre-B cells and κ/λ$^+$ immature B cells (FIG. 4E bottom left and top panels). These cells were µ$^+$δ$^-$, indicating that they were not mature B cells (FIG. 4E bottom right panel). All CD19$^+$ cells were also positive for Ig (FIG. 4F), as well as Igβ, suggesting that they are capable of signaling through their B-cell receptor or pre-B-cell receptor. These results showed that pro-B cells had been produced at week 3 to week 4 week of stage 2 and that a mixture of pre-B and immature B cells had been produced at the end of stage 2.

No significant difference was observed in the percentage of B cells derived among the experiments starting with HSPCs with no virus, HSPCs transduced with control vectors (mock or GFP vectors), or HSPCs transduced with b12 constructs (FIG. 5A). Also, neither MH-b12 nor EEK-b12 affected the development of CD19$^+$CD10$^+$ pre-B and CD19$^+$CD10$^-$ immature B cells at week 6 of stage 2 (FIG. 5B). All these results suggested that neither the expression of a secretory IgG nor the expression of GFP interferes with normal B-cell development in the bone marrow.

Example 3

Stage 3: Activation and Plasma Cell Differentiation of In Vitro-Developed Human B Cells In this example, B-cell activators, including IL-2, IL-10, and CpG DNA, were used in conjunction with MS5 cells expressing CD40L to support the activation and terminal differentiation of pro-B, pre-B, and immature B cells to plasmablast and plasma cells. Within 2-3 weeks of co-culturing with MS40L cells, about 90% of B-cells obtained from stage 2 developed into activated B cells including antibody-secreting plasmablasts (35-37%) and plasma cells (16-23%).

The human CD40L clone was subcloned into FUW. MS5 stromal cells were transduced by FUW-CD40L virus, and MS40L single clones were selected by flow cytometry to generate stable MS5 cell lines that express low or high levels of human CD40L on the cell surface (named MS40L-low and MS40-high cell lines, see FIG. 6A). Then, the pro-B, pre-B, and immature B cells generated during stage 2 were counted and seeded at 5×10$^4$ cells/500 µL per well in 48-well plates precoated with MS40L-low or MS40-high cells in the presence of 10 ng/mL of IL-2, 100 ng/mL of IL-10, and 2 µM CpG DNA (SEQ ID NO:3). In some experiments, IL-6 (50 ng/mL), soluble CD40L (1 µg/mL), and a cross-linking enhancer (2 µg/mL) were also used.

Figure 6:
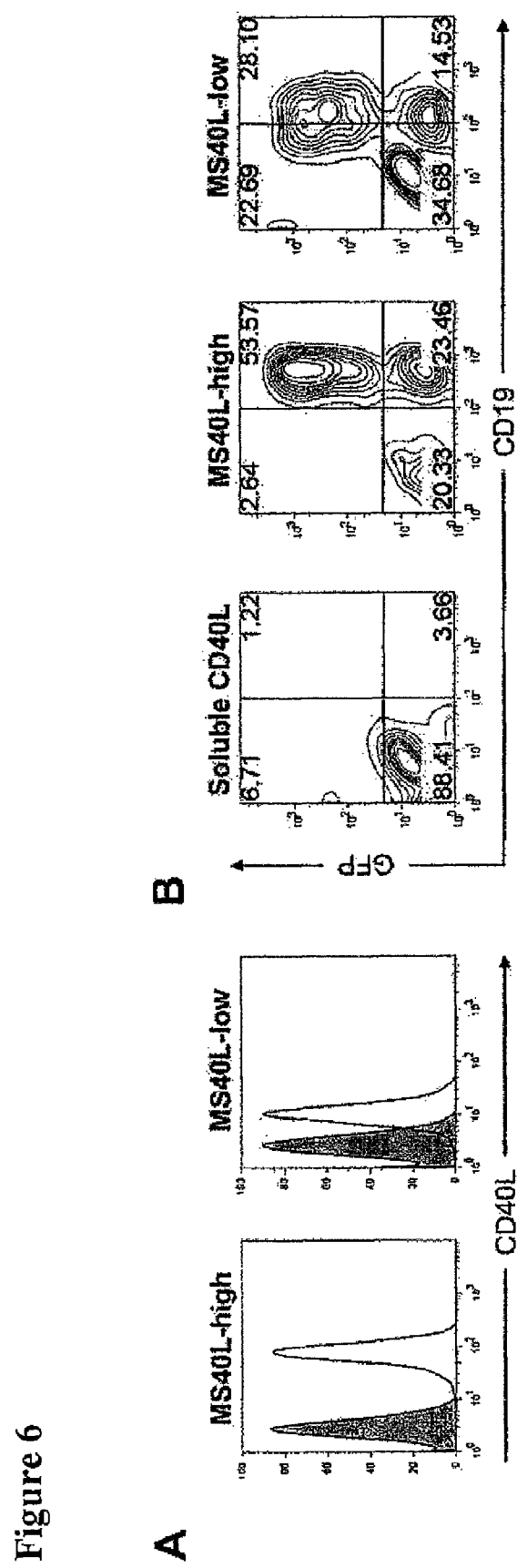
FIG. 6A shows expression levels of CD40L in two MS5 cell lines transduced by FUW-CD40L virus (MS40L-high and MS40L-low cell lines). The shaded peaks represent parental MS5 cells, and the open peaks represent transduced cells.
FIG. 6B shows the abilities of soluble CD40L (1 μg/mL) and two MS40L stable lines (MS40L-high and MS40L-low) in supporting B-cell activation. The stage 2-derived cells were incubated in the presence of IL-2 (10 ng/mL), IL-10 (100 ng/mL), and CpG DNA (SEQ ID NO:3, 2 μM) for 18 days. Soluble CD40L did not support the survival of B cells, leading to nearly no detection of CD19$^+$GFP$^+$ cells. In contrast, both of the MS40L cell lines supported the survival and expansion of B cells.
FIG. 6C shows the comparison between the ability of MS40L-high in inducing plasma cell differentiation and that of MS40L-low as indicated by decreased CD19 and surface IgM expression (top panels), appearance of CD20$^-$CD38$^+$ cells (middle panels), and increased CD27 expression (bottom panels).
FIG. 6D shows flow cytometric analysis of plasma cell differentiation. Naive B cells isolated from human peripheral blood were cultured in the presence of MS40L-low and the indicated stimuli (CpG, IL-2, IL-10, and/or IL-6 [50 ng/mL]) for 9 days and stained for flow cytometric analysis of plasma cell differentiation (middle panels, CD20$^-$CD38$^+$ cells; right panels, CD19$^-$CD27$^+$ and CD19$^{low}$CD27$^{+/high}$ cells).
Figure 6:
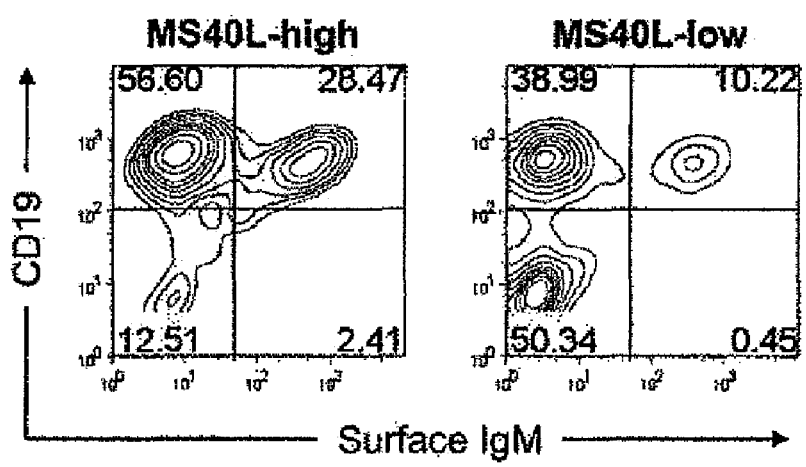
Figure 6:
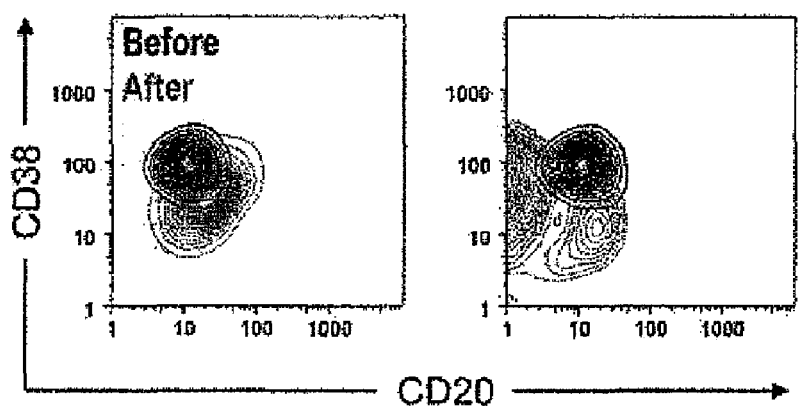
Figure 6:
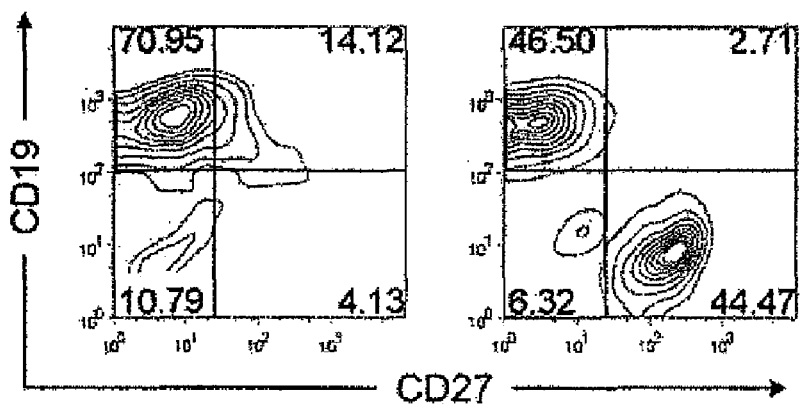
Figure 6:
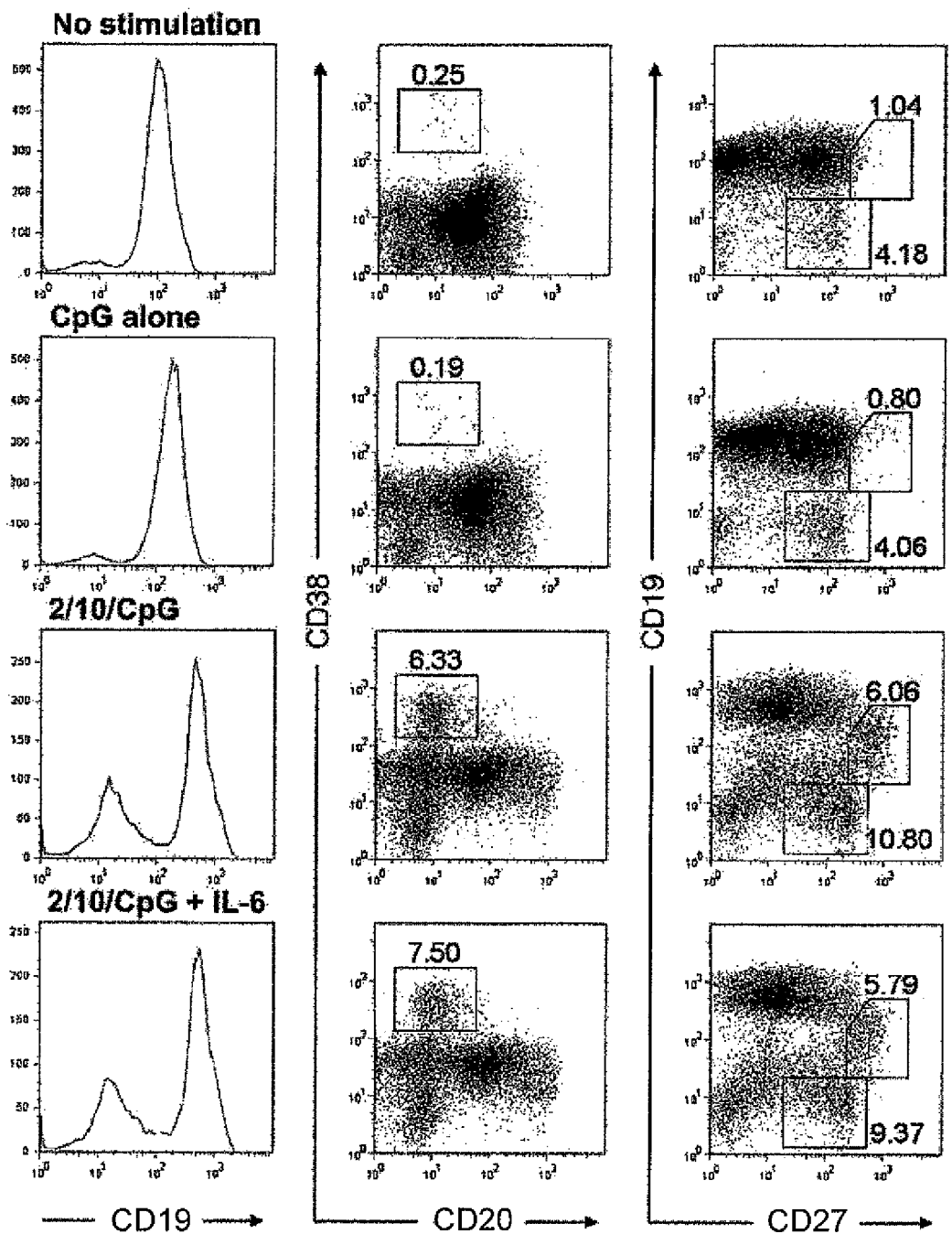

Soluble CD40L failed to promote the survival and differentiation of in vitro-derived B cells. On the other hand the anchored 40L provided by the MS40L-high or MS40L-low cell lines are potent in the activation and proliferation of in vitro-derived B cells as compared with soluble CD40L. Also, MS40L-low cells were more potent than MS40L-high in inducing stage 2-derived B cells to become plasma cells (FIG. 6B). Plasma cells, which were most evident at the end of stage 3, were defined by a reduced level of surface CD19 and IgM (FIG. 6C top panels), appearance of CD20$^-$CD38$^+$ cells (FIG. 6C middle panels), and an increased level of CD27 (FIG. 6C bottom panels). These results showed that a suitable level of anchored CD40L could induce proliferation and terminal differentiation of in vitro-derived B cells into plasma cells.

To achieve antigen-independent activation of naive B cells, different stimulatory combinations including cytokines selected from CpG, IL-2, IL-10, IL-15, IL-6, interferon-α, and anti-CD40L, were tested for the activation of naive B cells isolated from human peripheral blood with different stimulatory combinations. In one set of experiments, combinations of IL-2/IL-10/CpG and IL-2/IL-10/CpG/IL-6 were used and administered to the cells once every 3 days. Both of the combinations increased the percentages of antibody-secreting CD20$^-$CD38$^+$ and CD19$^{-/low}$CD27$^+$ cells (FIG. 6D).

A detailed phenotypic evaluation of stage 3 cells cultured for 2 to 3 weeks on MS40L-low in the presence of IL-2, IL-10, and CpG revealed that antibody-secreting plasmablasts and plasma cells were generated. During the differentiation of stage 3 cells, CD19 expression decreased (FIG. 7A left panels), whereas the percentages of $CD20^-CD38^+$ cells (precursor and definitive plasma cells) and $CD138^+$ plasma cells increased (FIG. 7B). CD86 expression was elevated shortly after the initiation of stage 3 (FIG. 7A left panels); however, the enhanced CD86 level decreased as B cells switched from proliferating to differentiating into plasma cells. Surface IgG expression appeared, whereas the percentage of $CD27^+$ cells increased (FIG. 7C), indicating the occurrence of class switching of endogenous IgM to membrane-bound IgG and the appearance of the memory cell phenotype. No difference was observed between the plasma cell differentiation of B cells carrying GFP (FIG. 8) or b12 lentiviral constructs, and the effects of MH and EEK promoters on the plasma cell phenotype did not differ (FIG. 7A-B), suggesting that the expression of the secretory IgG transgene did not interfere with plasma cell differentiation.

B cells at the end of stage 3 were larger and more granular than the cells generated from stage 2 (FIG. 7E), displayed the morphology of plasmablasts or plasma cells (FIG. 7F; for a histologic comparison to normal plasmablasts and plasma cells from human bone marrow, see FIG. 9), and produced large amounts of endogenous IgM, IgG, and IgA (FIG. 7G). These results above showed that stage 2-derived B cells can be activated to reach the stage of plasmablasts and plasma cells using a combination of IL-2, IL-10, CpG, and MS40L-low and that these antibody-secreting cells were phenotypically and functionally normal regardless of the presence of transgenic $b12-IgG_1$.

Example 4

Programming of Human B Cells to Produce Anti-HIV Antibody $b12-IgG_1$

Analysis of the integrated lentivirus in genomic DNA of B cells at different time points of the in vitro culture system revealed that the provirus was present throughout B-cell development (FIG. 10). The cells carrying the integrations apparently survived and developed, as the provirus copy numbers per cell at the end of stage 3, on average, were not statistically different from those of their progenitors (P=0.26). This suggested that stable integration of the lentivirus encoding the anti-HIV neutralizing antibody could be maintained from HSPCs to antibody-secreting B cells.

b12-specific ELISA was used to determine the amount of b12 secretion from cells generated during stage 2 and stage 3. During stage 2, a small amount of $b12-IgG_1$ was detected in weekly harvested cell culture supernatants if the b12 transgene had been introduced to the cells (FIG. 11A). The ubiquitin promoter drove a constantly low level of b12 expression. The expression of b12 in response to the MH promoter was also low but probably coincided with the time when pro-B cells started to appear. At the end of stage 3, high levels of endogenous IgM, IgG, and IgA were detected (FIG. 11B), and more than 100 ng/mL of b12 were detected if the cells were originally transduced with MH-b12, and a higher level of nearly 1.5 μg/mL of b12 in the case of EEK-b12 (FIG. 11C). Consistently, the EEK promoter was more active than the MH promoter in driving GFP expression in a plasmacytoma cell line (FIG. 11F), but not in either Nalm-6 or Ramos cell lines, suggesting that a light chain promoter may preferentially drive the expression of b12 in antibody-secreting plasma cells.

The ubiquitin promoter was relatively weak for driving transgenes in B cells and thus failed to induce a level of $b12-IgG_1$ comparable with either of the two B cell-specific promoters. The capacity of a plasma cell's antibody secretion machinery may have limited the total amount of antibody secreted, leading to the reduction of IgM production from cells carrying EEK-b12 (FIG. 11B), when $b12-IgG_1$ was highly produced from these cells (FIG. 11C). $B12-IgG_1$ was also detectable in the cytoplasm of B cells carrying the transgene using intracellular costainings of fluorochrome-labeled $gp120_{MN}$ and anti-IgG interacting with the anti-gp120 epitope and heavy chain constant region of $b12-IgG_1$, respectively (FIG. 11D). The concentration of 1.5 μg/mL achieved by EEK-b12 was comparable with that of endogenous IgG production (about 1 μg/ml) and, when put into human serum, is enough to achieve more than 90% neutralization of HIV-1 virus in vitro. Collectively, these results showed that, by transducing HSPCs with MH-b12 or EEK-b12 lentiviral constructs and differentiating the transduced cells along B-lineage, human B cells could be programmed to produce the $b12-IgG_1$ neutralizing antibody.

Example 5

Development of Ig-Secreting Human B Cells from Unprimed HSPCs $CD34^+$ cells from human cord blood are seeded and cultured on MS5 murine stromal cell monolayer that expresses the B-lineage growth factor IL-7. The cell culture is fed biweekly, once with the additional fresh medium and once by aspiration of 80% of the medium in the culture well and addition of fresh medium. The cell culture is monitored for emergence of $CD19^+$ cells. When a significant percentage of the cell population become $CD34^-CD19^+$, the long-term cultured cells are harvested and enriched for $CD19^+$ cells using the MiniMacs cell separation system.

The enriched $CD19^+$ cells are then cultured in the presence of B-cell activators, including IL-2, IL-10, and CpG, in conjunction with MS5 cells expressing CD40L (such as MS40L-low and MS40L-high), as described in Example 3. It is expected that the MS5 cells will support the activation and terminal differentiation of the $CD19^+$ cells to Ig-secreting plasmablasts or plasma cells.

Example 6

Development of Antibody-Producing Human B Cells from Pro-B, Pre-B and/or immature B Cells Pro-B, pre-B, or immature B cells are seeded and cultured on MS5 murine stromal cell monolayer that expresses the B-lineage growth factor IL-7. The cell culture is fed biweekly, once with the additional fresh medium and once by aspiration of 80% of the medium in the culture well and addition of fresh medium. The cell culture is monitored for enrichment of $CD19^+\mu^+\delta^+$ cells. When a significant percentage of the cell population become $CD19^+\mu^+\delta^+$, the cells are harvested and enriched for $CD19^+\mu^+\delta^+$ cells using the MiniMacs cell separation system.

Genes encoding an antibody of interest are then introduced into the enriched $CD19^+\mu^+\delta^+$ cells by conventional gene delivery techniques such as transfecting the cells with lentiviral vectors that contain genes encoding the antibody of interest. The $CD19^+\mu^+\delta^+$ cells that contain genes encoding the antibody of interest are cultured in the presence of B-cell activators, including IL-2, IL-10, and CpG DNA, in conjunction with MS5 cells expressing CD40L (such as MS40L-low and MS40L-high), as described in Example 3. It is expected that the MS5 cells will support the activation and terminal differentiation of the CD19$^+$μ$^+$δ$^+$ cells to plasmablasts or plasma cells that produce the antibody of interest.

Example 7

Development of Antibody-Producing Human B Cells from Naïve B Cells

Naïve B cells that are carries genes encoding an antibody of interest are seeded and cultured in the presence of B-cell activators, including IL-2, IL-10, and CpG DNA, in conjunction with MS5 cells expressing CD40L (such as MS40L-low and MS40L-high), as described in Example 3. The genes encoding the antibody of interest are introduced into the naïve B cells by conventional gene delivery techniques such as transfecting the naïve B cells with lentiviral vectors that contain genes encoding for the antibody of interest. It is expected that the MS5 cells will support the activation and terminal differentiation of the naïve B cells to plasmablasts or plasma cells that produce the antibody of interest.

Although the foregoing invention has been described in terms of certain embodiments, other embodiments will be apparent to those of ordinary skill in the art. Accordingly, other combinations, omissions, substitutions and modifications will be apparent to the skilled artisan, in view of the disclosure herein. Accordingly, the present application is not intended to be limited by the recitation of the preferred embodiments, but is instead to be defined by reference to the appended claims. All references cited herein are incorporated by reference in their entirety.

What is claimed is:

1. A method for generating a population of antibody-producing B cells in vitro, comprising:
   (a) contacting a population of hematopoietic stem/progenitor cells (HSPCs) in vitro with a polynucleotide delivery system, wherein the polynucleotide delivery system comprises a polynucleotide encoding an antibody of interest;
   (b) culturing the HSPCs in the presence of one or more B-cell priming factors;
   (c) co-culturing the HSPCs with a population of first supporting cells expressing one or more B-lineage growth factors until at least about 20% of the HSPCs become $CD19^+\mu^+$;
   (d) co-culturing the $CD19^+\mu^+$ cells obtained in step (c) with a population of second supporting cells expressing CD40L in the presence of one or more B-cell activators until at least about 20% of the $CD19^+\mu^+$ cells become B cells that produce the antibody of interest.

2. The method of claim 1, wherein the HSPCs are $CD34^+$ cells from cord blood.

3. The method of claim 1, wherein the HSPCs are primary bone marrow cells.

4. The method of claim 1, wherein at least one of one or more the B-cell priming factors is selected from the group consisting of IL-3, Flt3 ligand, thrombopoietin, stem cell factor (SCF), granulocyte colony-stimulating factor (G-CSF), granulocyte colony-stimulating factor (GM-CSF), IL-7, and IL-11.

5. The method of claim 1, wherein the B-cell priming factors are IL-3, Flt3 ligand, thrombopoietin, SCF, and G-CSF.

6. The method of claim 1, wherein the HSPCs are co-cultured with a population of first supporting cells expressing one or more B-lineage growth factors until at least about 30% of the HSPCs become $CD19^+\mu^+$.

7. The method of claim 1, wherein the first supporting cells are stromal cells.

8. The method of claim 7, wherein the first supporting cells are stromal cells expressing the B-lineage growth factors IL-7.

9. The method of claim 1, wherein at least one of the B-cell activators is selected from the group consisting of CpG DNA, IL-2, IL-10, IL-15, IL-6, IFNα, and anti-CD40L.

10. The method of claim 9, wherein the B-cell activators are CpG DNA, IL-2, and IL-10.

11. The method of claim 9, wherein one B-cell activators is CpG DNA.

12. The method of claim 1, wherein at least about 40% of the $CD19^+\mu^+$ cells obtained in step (b) are $CD19^+\mu^+V_{preB}^+$ pre-B cells or $CD19^+\mu^+\kappa/\lambda^+$ immature B cells.

13. The method of claim 1, wherein at least about 40% of the B cells that produce the antibody of interest are antibody-secreting plasmablasts and plasma cells.

14. The method of claim 1, the polynucleotide delivery system is a retroviral vector.

15. The method of claim 14, the retroviral vector is a lentiviral vector.

16. The method of claim 15, wherein the lentiviral vector comprises a B cell-specific promoter.

17. The method of claim 16, wherein the B cell-specific promoter is the EKK promoter.

18. A method for generating a population of antibody-producing B cells in vitro, comprising:
   (a) culturing a population of hematopoietic stem/progenitor cells (HSPCs) in the presence of one or more B-cell priming factors;
   (b) co-culturing the HSPCs with a population of first supporting cells expressing one or more B-lineage growth factors until at least about 20% of the HSPCs become $CD19^+\mu^+$;
   (c) co-culturing the $CD19^+\mu^+$ cells obtained in step (b) with a population of second supporting cells expressing CD40L in the presence of one or more B-cell activators until at least about 20% of the $CD19^+\mu^+$ cells become antibody-producing B cells.

19. The method of claim 18, wherein the B-cell priming factors are selected from IL-3, Flt3 ligand, thrombopoietin, SCF, and G-CSF.

20. A method for generating antibody-producing B cells, comprising:
- transfecting a population of target cells in vitro with a polynucleotide delivery system, where the polynucleotide delivery system comprises a polynucleotide encoding an antibody of interest;
- co-culturing the target cells with a population of supporting cells expressing CD40L in the presence of one or more B-cell activators until at least about 20% of the target cells become B cells that produce the antibody of interest.

21. The method of claim 20, wherein the target cells are selected from pro-B, pre-B, immature B and naïve B cells.

22. The method of claim 20, wherein at least one of the B-cell activators is selected from the group consisting of CpG DNA, IL-2, IL-10, IL-15, IL-6, IFNα, and anti-CD40L.

* * * * *

UNITED STATES PATENT AND TRADEMARK OFFICE
CERTIFICATE OF CORRECTION

PATENT NO. : 8,133,727 B2
APPLICATION NO. : 12/622379
DATED : March 13, 2012
INVENTOR(S) : Xin Luo et al.

It is certified that error appears in the above-identified patent and that said Letters Patent is hereby corrected as shown below:

At Page 1 (Item 56), Column 2, Line 25, Under Other Publications, after "DNA" insert --Activation--.

At Page 2 (Item 56), Column 2, Line 10, Under Other Publications, change "Ootential" to --Potential--.

In the Drawing

The drawing sheet 12 of 17 consisting of Fig(s) 8A and B should be deleted and substitute therefore the attached drawing sheet consisting of Fig(s) 8A and B.
At Sheet 12 of 17 (Fig. 8B), Line 7 (Approx.), Change "40" to --10--.

At Column 8, Line 61, Change "in" to --In--.

At Column 9, Line 53, Change "sill" to --still--.

At Column 13, Line 49, Change "acetamidate," to --acetimidate,--.

At Column 21, Line 61, Change "Trypanasoma," to --Trypanosoma,--.

At Column 23, Line 20, Change "SpectroMax" to --SpectraMax--.

At Column 23, Line 56, Change "constructis" to --constructs--.

At Column 34, Line 52 (Approx.), In Claim 17, Change "EKK" to --EEK--.

Signed and Sealed this
Eleventh Day of September, 2012

David J. Kappos
*Director of the United States Patent and Trademark Office*

SEQUENCE LISTING

```
<160> NUMBER OF SEQ ID NOS: 7

<210> SEQ ID NO 1
<211> LENGTH: 1272
<212> TYPE: DNA
<213> ORGANISM: Artificial Sequence
<220> FEATURE:
<223> OTHER INFORMATION: MH promoter

<400> SEQUENCE: 1
ggattgttta tcttaggagg catgcttact gttaaaagac aggatatgtt tgaagtggct      60
tctgagaaaa atggttaaga aaattatgac ttaaaaatgt gagagatttt caagtatatt     120
aattttttta actgtccaag tatttgaaat tcttatcatt tgattaacac ccatgagtga     180
tatgtgtctg gaattgaggc caaagcaagc tcagctaaga aatactagca cagtgctgtc     240
ggccccgatg cgggactgcg ttttgaccat cataaatcaa gtttatttt ttaattaatt      300 gagcgaagct ggaagcagat gatgaattag agtcaagatg gctgcatggg ggtctccggc     360
acccacagca ggtggcagga agcaggtcac cgcgagagtc tatttagga agcaaaaaaa      420 cacaattggt aaatttatca cttctggttg tgaagaggtg gttttgccca ggcccagatc     480
tgaaagtgct ctactgagca aaacaacacc tggacaattt gcgtttctaa aataaggcga     540
ggctgaccga aactgaaaag gctttttta actatctgaa tttcatttcc aatcttagct     600
tatcaactgc tagtttgtgc aaacagcata tcaacttcta aactgcattc attttaaag     660 taagatgttt aagaaattaa acagtcttag ggagagttta tgactgtatt caaaaagttt     720
tttaaattag cttgttatcc cttcatgtga taactaatct caaatacttt ttcgatacct     780
cagagcatta ttttcataat gactgtgttc acaatctttt taggttaact cgttttctct     840
ttgtgattaa ggagaaacac tttgatattc tgatagagtg gccttcattt tagtattttt     900
caagaccact tttcaactac tcactttagg ataagtttta ggtaaaatgt gcatcattat     960
cctgaattat ttcagttaag catgttagtt ggtggcataa gagaaaactc aatcagatag    1020
gtaccgcggg cccgggatcc gcaggattta gggcttggtc tctcagcatc ccacacttgt    1080
acagctgatg tggcatctgt gttttctttc tcatcctaga tcaggctttg agctgtgaaa    1140
taccctgcct catgcatatg caaataacct gaggtcttct gagataaata tagatatatt    1200
ggtgccctga gagcatcaca taacaaccac attcctcctc tgaagaagcc cctgggagca    1260
cagctcatca cc                                                        1272
```

<210> SEQ ID NO 2
<211> LENGTH: 904
<212> TYPE: DNA
<213> ORGANISM: Artificial Sequence
<220> FEATURE:
<223> OTHER INFORMATION: EEK promoter

<400> SEQUENCE: 2

```
taaaccggtg agtttcatgg ttacttgcct gagaagatta aaaaaagtaa tgctacctta      60
tgagggagag tcccagggac caagatagca actgtcatag caaccgtcac actgctttgg     120
tcaaggagaa gacccttttgg ggaactgaaa acagaaccttt gagcacatct gttgctttcg    180
ctcccatcct cctccaacag ggctgggtgg agcactccac acccttttcac cggtcgtacg    240 gctcagccag agtaaaaatc acacccatga cctggccact gagggcttga tcaattcact    300
ttgaatttgg cattaaatac cattaaggta tattaactga ttttaaaata agatatattc    360
gtgaccatgt ttttaacttt caaaaatgta gctgccagtg tgtgatttta tttcagttgt    420
acaaaatatc taaacctata gcaatgtgat taataaaaac ttaaacatat tttccagtac    480
cttaattctg tgataggaaa attttaatct gagtatttta atttcataat ctctaaaata    540
gtttaatgat ttgtcattgt gttgctgtcg tttacccccag ctgatctcaa aagtgatatt    600
taaggagatt attttggtct gcaacaactt gatagggctc agcctctccc acccaacggg    660
tggaatcccc cagaggggga tttccaagag gccacctggc agttgctgag ggtcagaagt    720
gaagctagcc acttcctctt aggcaggtgg ccaagattac agttgacccg tacgtgcagc    780
tgtgcccagc ctgccccatc ccctgctcat ttgcatgttc ccagagcaca acctcctgcc    840
ctgaagcctt attaataggc tggtcacact ttgtgcagga gtcagactca gtcaggacac    900
agct                                                                   904
```

<210> SEQ ID NO 3
<211> LENGTH: 24
<212> TYPE: DNA
<213> ORGANISM: Artificial Sequence
<220> FEATURE:
<223> OTHER INFORMATION: CpG DNA

<400> SEQUENCE: 3

```
tcgtcgtttt gtcgttttgt cgtt                                              24
```

<210> SEQ ID NO 4
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 4

```
tcccagctac tggggaggct gagg                                              24
```

<210> SEQ ID NO 5
<211> LENGTH: 19
<212> TYPE: DNA
<213> ORGANISM: Artificial Sequence
<220> FEATURE:

```
<223> OTHER INFORMATION: Synthetic polynucleotide

<400> SEQUENCE: 5
gagtcctgcg tcgagagag                                                19

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
tgtgtgcccg tctgttgtgt                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 7
gagtcctgcg tcgagagagc                                               20
```